US012788568B2

(12) United States Patent
Vogt et al.

(10) Patent No.: US 12,788,568 B2
(45) Date of Patent: Nov. 10, 2026

(54) DEVICE AND METHOD FOR PRODUCING SPACERS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 412 days.

(21) Appl. No.: 17/378,313

(22) Filed: Jul. 16, 2021

(65) Prior Publication Data

US 2022/0015911 A1 Jan. 20, 2022

(30) Foreign Application Priority Data

Jul. 17, 2020 (EP) .................................... 20186551

(51) Int. Cl.
*A61F 2/30* (2006.01)
*A61F 2/32* (2006.01)
(Continued)

(52) U.S. Cl.
CPC ............ *A61F 2/30942* (2013.01); *A61F 2/32* (2013.01); *A61F 2/38* (2013.01); *A61F 2/40* (2013.01);
(Continued)

(58) Field of Classification Search
CPC ....... A61F 2002/30957; A61F 2/30942; B29C 33/0055; B29C 70/70; B65D 51/18; B65D 51/28; A47G 19/26; A47G 23/0233
See application file for complete search history.

(56) References Cited

U.S. PATENT DOCUMENTS 5,681,289 A 10/1997 Wilcox et al.
6,245,111 B1 6/2001 Shaffner
(Continued)

FOREIGN PATENT DOCUMENTS

AU 2008246286 B2 * 8/2015
DE 102015104704 B4 10/2016
(Continued)

OTHER PUBLICATIONS

Biomaterials Innovation Teknimed: Acrylic Bone Cement: CemFix 1&3, XP055758318, URL: http://www.innovamed.uy/media/file/60, Jan. 1, 2014.
(Continued)

*Primary Examiner* — Susan D Leong
*Assistant Examiner* — Timothy G Hemingway
(74) *Attorney, Agent, or Firm* — Dicke, Billig & Czaja, PLLC

(57) ABSTRACT

The invention relates to a device for producing a spacer having a casting mold lower part (1) with a cavity (2), a casting mold wall (3) which extends peripherally away from an edge of the cavity (2) and which is open on the opposite side, a casting mold upper part (5) with a shaping surface (6), wherein the casting mold upper part (5) can be inserted into an interior (4) of the casting mold lower part (1) and is displaceable in the direction of the cavity (2), such that a hollow space is formed which is delimited by the cavity (2), the shaping surface (6) and the casting mold wall (3) and in which the spacer is moldable, at least one container (7) for receiving excess bone cement paste, and at least one opening (8) in the shaping surface (6) and/or in the cavity (2), which opens into the at least one container (7) for receiving excess bone cement paste.
The invention also relates to a method for producing spacers using such a device.

25 Claims, 35 Drawing Sheets

(51) Int. Cl.
*A61F 2/38* (2006.01)
*A61F 2/40* (2006.01)

(52) U.S. Cl.
CPC ............... *A61F 2002/30449* (2013.01); *A61F 2002/30451* (2013.01); *A61F 2002/30672* (2013.01); *A61F 2002/30957* (2013.01); *A61F 2310/00011* (2013.01); *A61F 2310/00353* (2013.01)

(56) References Cited

U.S. PATENT DOCUMENTS

| | | | | |
|---|---|---|---|---|
| 6,361,731 | B1 * | 3/2002 | Smith | B29C 33/405 264/318 |
| 7,637,729 | B2 | 12/2009 | Hartman et al. | |
| 7,789,646 | B2 | 9/2010 | Haney et al. | |
| 8,480,389 | B2 | 7/2013 | Haney et al. | |
| 8,801,983 | B2 | 8/2014 | Haney et al. | |
| 8,900,322 | B2 | 12/2014 | De Beaubien | |
| 9,433,506 | B2 | 9/2016 | Lomicka et al. | |
| 10,071,511 | B2 | 9/2018 | Smith et al. | |
| 2007/0222114 | A1 | 9/2007 | Ziran et al. | |
| 2010/0042213 | A1 | 2/2010 | Nebosky et al. | |
| 2010/0102484 | A1 | 4/2010 | Haney et al. | |
| 2011/0015754 | A1 | 1/2011 | Leonard et al. | |
| 2012/0256344 | A1 | 10/2012 | Stolarski et al. | |
| 2014/0159282 | A1 | 6/2014 | Smith et al. | |
| 2016/0129610 | A1 | 5/2016 | Cappelletti | |
| 2016/0332328 | A1 | 11/2016 | Wuest et al. | |
| 2018/0021075 | A1 * | 1/2018 | Vogt | B05C 17/00576 606/94 |
| 2018/0132919 | A1 * | 5/2018 | Vogt | A61M 5/285 |
| 2019/0290833 | A1 | 9/2019 | Vogt et al. | |

FOREIGN PATENT DOCUMENTS

| | | | | |
|---|---|---|---|---|
| DE | 102017110732 | A1 | 11/2018 | |
| EP | 2522310 | A1 | 11/2012 | |
| EP | 1985317 | B1 | 6/2013 | |
| EP | 2617393 | B1 | 7/2015 | |
| EP | 1991170 | B1 | 10/2016 | |
| EP | 2931180 | B1 | 11/2016 | |
| EP | 2818138 | B1 | 3/2017 | |
| EP | 2787928 | B1 | 7/2017 | |
| EP | 2532323 | B1 | 2/2018 | |
| EP | 3075357 | B1 | 8/2018 | |
| EP | 3143963 | B1 | 11/2018 | |
| EP | 3215064 | B1 * | 3/2020 | A61F 2/30724 |
| EP | 3881802 | A1 | 9/2021 | |
| EP | 3881803 | A1 | 9/2021 | |
| GB | 1388115 | A * | 3/1975 | B29C 37/0085 |
| JP | 2016/500292 | | 1/2016 | |
| JP | 2016187552 | | 11/2016 | |
| JP | 2017533741 | | 11/2017 | |
| KR | 20190070524 | A * | 11/2019 | B65D 43/0212 |
| WO | 2009073781 | A2 | 6/2009 | |
| WO | 2016/071939 | | 5/2016 | |
| WO | 2016205077 | A1 | 12/2016 | |
| WO | 2017178951 | A1 | 10/2017 | |

OTHER PUBLICATIONS

Geek Gaming Scenics Rock Moulds Your Questions Answered: How to Use Woodland Scenics Rock Moulds, XP054981183, URL:https://www.youtube.com/watch?v=1kxrxvwq0pk, Apr. 17, 2018.
Luke Towan “Build an Ultra-Realistic River in the Alaskan Wilderness” . . . Realistic Scenery vol. 21, XP054981182, https://www.youtube.com/watch?v=nCZVovoGonM, Jan. 8, 2020.
Search Report for priority European Patent Application No. 20186551.6 mailed Dec. 17, 2020 by the European Patent Office.

* cited by examiner

DEVICE AND METHOD FOR PRODUCING SPACERS

CROSS-REFERENCE TO RELATED APPLICATIONS

This application claims priority to European Patent Application No. 20186551.6, filed on Jul. 17, 2020, the entirety of which is incorporated herein by reference.

The invention relates to a device for producing a spacer by curing bone cement paste in a casting mold, wherein the spacer is provided to temporarily replace a joint or part of a joint comprising an articulating surface of the joint in the medical field, in particular to temporarily replace a hip joint, a knee joint or a shoulder joint. The spacer is provided as a temporary placeholder in medical applications for temporarily replacing a joint or part of a joint comprising an articulating surface of the joint. The spacer is preferably suitable and provided for temporarily replacing a hip joint, a knee joint or a shoulder joint. The device is accordingly preferably provided for producing a hip joint spacer, a knee spacer or a shoulder joint spacer. The invention also relates to a method for producing such a spacer using such a device.

The present invention accordingly in particular provides a device for the intraoperative production of hip, shoulder and knee spacers which are intended as temporary placeholders (spacers) for the interim phase in the context of two-stage revisions of infected hip, shoulder and knee total joint endoprostheses. The device is suitable for producing spacers with low-viscosity and high-viscosity polymethyl methacrylate bone cement paste. The present invention also provides a method for producing spacers using the device.

Joint endoprostheses, such as hip joint endoprostheses, knee joint endoprostheses and shoulder joint endoprostheses, are widely implanted worldwide. Unfortunately, in a small percentage of cases, joint endoprostheses are colonized by microbial microorganisms, in particular Gram-positive bacteria and also Gram-negative bacteria, and to a very small extent by yeasts and fungi. These microbial microorganisms, mainly typical skin microbes such as *Staphylococcus aureus* and *Staphylococcus epidermidis*, may enter a patient's body during a surgical operation (OP). It is also possible for microbial microorganisms to enter joint endoprostheses hematogenically. When joint endoprostheses are colonized by microbial microorganisms, the surrounding bone and soft tissue also become infected and damaged by the microbial microorganisms.

The prior art primarily encompasses two treatment methods for infected joint endoprostheses, one-stage septic revision and two-stage septic revision. In the case of one-stage revision, the infected joint endoprosthesis is removed first, next radical debridement is performed and then a revision joint endoprosthesis is implanted within one OP.

A hip joint spacer consists of a stem, a collar, a neck and a ball head and replicates hip joint endoprostheses in shape and size. Similarly, a shoulder joint spacer replicates a shoulder joint endoprosthesis in shape and size. A knee spacer has a tibial component and a femoral component and basically replicates the shape and size of the knee joint endoprosthesis. The tibial component has a stem and tibial plateau, wherein the tibial plateau forms a sliding or rolling surface of the knee joint and the stem can be anchored in the tibia. The femoral component has a stem for anchoring in the femur and two condyles for rolling on the tibial plateau. The tibial component and femoral component are anchored with bone cement to the respective bones, i.e. for example in the case of the femoral component to the distal femur or in the femoral canal and in the case of the tibial component with the stem to the proximal tibia or in the tibial canal.

The spacer is anchored with bone cement to the respective bone, i.e. for example in the case of hip joint spacers to the proximal femur or in the femoral canal. The spacer remains for up to several weeks in the patient until the inflammation has subsided and clinical inflammation markers have receded. The spacer is then removed in a second OP and a revision joint endoprosthesis implanted after fresh debridement.

With spacers, antibiotics are added to the cement powder before actual spacer production. Using this antibiotically modified bone cement powder, a bone cement paste is then produced by admixing monomer liquid and spacers are cast from this bone cement paste which then cure by polymerization with the assistance of the monomer liquid added to the cement powder. The bone cement paste thus substantially incorporates the antibiotics. The antibiotic particles situated in areas close to the surface are released under the action of bodily fluids, such as wound secretions. Active ingredient release is greatest at the start and then diminishes over the course of several days.

US 2010/0042213 A1 discloses a hip joint prosthesis with a reservoir for liquid inside the implant. A hip spacer is known from WO 2017/178951 A1 which has indentations, wherein a substance for treating the bone may be introduced into the indentations. U.S. Pat. No. 6,245,111 B1 proposes a hip joint prosthesis, the surfaces of which are coated with an antibiotic. U.S. Pat. No. 5,681,289 discloses a device for distributing a liquid active ingredient with the assistance of a bladder inside the device. EP 1 991 170 B1 and US 2011/0015754 A1 describe a hip joint spacer containing active ingredients. US 2019/0290833 A1 discloses an irrigatable hip joint spacer, with which a liquid circuit can be created. WO 2016/205077 A1 and U.S. Pat. No. 8,900,322 B2 describe further spacers with an irrigation function.

In two-stage septic revisions, in a first OP the infected joint endoprosthesis is initially removed, then debridement is performed and thereafter a spacer is implanted. Spacers are of major significance as temporary placeholders in the interim phase in the context of two-stage septic replacement operations for knee, hip and shoulder total joint endoprostheses. During intraoperative production of these spacers, medical staff may, depending on the available antibiogram of the microbial microorganisms responsible for the infection, add to the polymethyl methacrylate (PMMA) bone cement one or more antibiotic(s) specifically tailored to the microorganisms. Such a bone cement is known for example from EP 1 985 317 B1. Resin casting molds are conventional for the intraoperative production of spacers with polymethyl methacrylate bone cement. Such casting molds are for example known from patents EP 2 617 393 B1 and EP 3 075 357 B1, and from European patent applications EP 20 164 534 and EP 20 164 541 which are not prior publications. A heatable casting mold is known from patent EP 2 818 138 B1.

Spacers may on the one hand be produced by the OP personnel during the OP itself from PMMA bone cement powder, antibiotics and monomer liquid, for example with a spacer mold, as described for example in patents DE 10 2015 104 704 B4 or EP 2 617 393 B1; on the other hand it is also conventional to use spacers prefabricated industrially from bone cement. Resin casting molds for intraoperative production of one-part hip spacers are described in U.S. Pat. No. 6,361,731 B1. These casting molds are transparent and have two separate filling openings. As a result, even high-viscosity bone cement paste can be introduced into the casting mold with little pressure, because the flow paths for the bone cement paste are relatively short. When using non-high-viscosity bone cement paste, the risk arises, once filling of the casting mold is complete, of bone cement paste flowing back out of the filling openings before curing begins.

In a further development, patents U.S. Pat. Nos. 7,637,729 B2, 7,789,646 B2, 8,480,389 B2 and 8,801,983 B2 propose multipart casting molds for the production of modular hip spacers. These modular hip spacers consist of a spacer head and a separate stem. One casting mold is therefore needed for the spacer head and a separate casting mold for the stem. The casting mold for the stem is in one piece and has a thread at the filling opening for connecting the casting mold to a cement cartridge containing the bone cement paste. Such modular systems have to be individually assembled to the correct size and the parts connected together so that they are capable of withstanding the pressure on injection of the often high-viscosity bone cement paste. Multipart casting molds are accordingly costly and also complicated to use.

U.S. Pat. No. 7,789,646 B2 describes a casting mold in which the filling opening of the casting mold can be closed using a plug once the bone cement paste has been introduced into the casting mold. Before that, however, the casting mold has to be unscrewed from the cement cartridge. When using low-viscosity cement paste, it is therefore possible, if the casting mold is held in an unfavorable way, for cement paste to run out during separation of the casting mold from the cement cartridge before the plug has been screwed in. When using high-viscosity bone cement paste, the same risk basically applies since the pressure required for filling causes elastic deformation of the casting mold which, when the casting mold returns to its shape, can press the bone cement paste which is inside back out of the open filling opening.

US 2007/0222114 A1 describes a hip spacer mold. This spacer mold consists of a plurality of mold segments which are connected together. Thanks to the plurality of segments, the spacer mold may be adapted very precisely to the patient's anatomical circumstances. The spacer mold segments are joined together by means of worm drive hose clips. A PMMA bone cement paste (polymethyl methacrylate bone cement paste) is introduced through channels in the spacer mold. The complex structure of the casting mold makes it very complicated to join the spacer mold segments together and to remove the hip spacer once curing of the PMMA bone cement paste is complete.

WO 2009/073 781 A2 proposes a spacer mold for a hip spacer consisting of two parts which may be displaced relative to one another in order to enable adaptation of the length of the stem. A further casting mold is disclosed in EP 2 522 310 A1. This device consists of at least two parts, wherein an insertion portion is arranged in a first part and an insertion receptacle is arranged in the second part. The two parts can be inserted into one another and form a casting mold for producing the stem of the hip spacer. EP 2 787 928 A1 describes a complex casting mold. This enables the production of hip spacers with different ball heads. The elements of the casting mold are fixed in place using connecting elements. U.S. Pat. No. 7,789,646 B2 describes a casting mold in which the filling opening of the casting mold can be closed using a plug once the bone cement paste has been introduced into the casting mold. Before that, however, the casting mold has to be unscrewed from the bone cement cartridge. When using non-high-viscosity bone cement paste, it is therefore possible, if the casting mold is held in an unfavorable way, for bone cement paste to run out during separation of the casting mold from the bone cement cartridge before the plug has been screwed in or inserted.

Documents EP 2 931 180 B1, US 2010/0102484 A1 and EP 2 532 323 B1 disclose bone cement molds for producing a tibial component of a knee spacer which is suitable for delivery of antibiotics. Assembling the mold parts and fixing them together involves considerable effort, however. In addition, due to the necessary components, the casting molds are complex, not inexpensive, and complicated to use. Patent EP 3 143 963 B1 discloses a three-part spacer mold with a tibial spacer mold, a femoral spacer mold and a third mold for producing a component which fills an intramedullary canal.

U.S. Pat. No. 10,071,511 B2 discloses casting molds for producing tibial components of knee spacers. Tibial components of differing heights may be fabricated using these casting molds. The casting mold consists of a lower part and an upper part which form a hollow space into which a polymethyl methacrylate bone cement paste may be injected via a port. The height of the tibial component to be cast is defined by a latch mechanism with teeth which sets the distance between the lower part and the upper part of the casting mold.

A similar concept is known from U.S. Pat. No. 9,433,506 B2 which claims a mold for a knee spacer. The casting mold here contains a port which, after demolding, is present as a stem in the intramedullary space. The casting mold is filled via the port with the assistance of a cement cartridge.

The object of the present invention is thus to overcome disadvantages of the prior art. In particular, the object of the invention is the development of an inexpensive device which is usable with the least possible effort for producing a spacer by curing bone cement paste in a casting mold and in the development of a method which can be carried out simply and inexpensively for producing a spacer by curing bone cement paste in a casting mold, with which one-part spacers, in particular hip, knee and shoulder spacers, can be produced by medical personnel in the operating room using bone cement paste, in particular polymethyl methacrylate bone cement.

The object of the present invention is accordingly to develop an inexpensive, simple to produce device with which medical personnel staff in the operating room can very straightforwardly produce articulating knee, hip and shoulder spacers and the tibial and femoral components of knee spacers using polymethyl methacrylate bone cement. Hip and shoulder spacers are of similar construction. They consist of a stem and a spacer head. A metal core may be or have been arranged inside the hip and shoulder spacer for the purpose of mechanical stabilization. The knee spacers consist of a tibial and a femoral component. It should be possible to produce spacers using not only low or non-high-viscosity but also high-viscosity (polymethyl methacrylate) bone cement paste.

The device should preferably be configured such that no cementing systems based on expellable cartridges are necessary for producing the spacers. It is intended to be possible to use bone cement paste mixed manually in a mixing bowl with a mixing spatula for producing the spacers. It should preferably be possible to fill the device without using cartridge expulsion devices. Contamination of the medical personnel and the operating room environment by any emerging excess bone cement paste should be avoided as far as possible.

The objects of the invention are achieved by a device for producing a spacer by curing bone cement paste in a casting mold, wherein the spacer is provided to temporarily replace a joint or part of a joint comprising an articulating surface of the joint in the medical field, in particular to temporarily replace a hip joint, a knee joint or a shoulder joint, the device having a casting mold lower part, wherein the casting mold lower part has a cavity for receiving a bone cement paste and for molding a first surface region of the spacer from the bone cement paste;

a casting mold wall which extends peripherally from a peripheral edge of the cavity of the casting mold lower part away from the cavity and which is open on the side opposite from the cavity, such that the cavity is accessible through an interior delimited by the casting mold wall;

a casting mold upper part, wherein the casting mold upper part has a shaping surface for molding a second surface region of the spacer from the bone cement paste, wherein the casting mold upper part is insertable through the open side of the casting mold wall opposite from the cavity into the interior and is displaceable in the direction of the cavity, such that a hollow space is formed which is delimited by the cavity of the casting mold lower part, the shaping surface of the casting mold upper part and the casting mold wall and in which the spacer is moldable;

at least one container for receiving excess bone cement paste; and at least one opening in the shaping surface of the casting mold upper part and/or in the cavity of the casting mold lower part, wherein the at least one opening opens into the at least one container for receiving excess bone cement paste, wherein the device has one or two lid(s) with which the casting mold upper part is closed or closable to the outside on the side opposite from the shaping surface of the casting mold upper part, such that an upper container closed to the outside is formed as one of the at least one containers for receiving bone cement paste between the casting mold upper part and the lid and/or with which the casting mold lower part is closed or closable to the outside on the side opposite from the cavity of the casting mold lower part, such that a lower container closed to the outside is formed as one of the at least one containers for receiving bone cement paste between the casting mold lower part and the lid and the lid or one of the lids is placed or placeable into or onto the casting mold upper part or into or onto the internal wall of the casting mold upper part in order to close the side opposite from the shaping surface of the casting mold upper part to the outside and there form a closed container for receiving excess bone cement paste, and/or the lid or one of the lids is placed or placeable into or onto the casting mold lower part in order to close the side opposite from the cavity of the casting mold lower part to the outside and there forms a closed container for receiving excess bone cement paste.

It may preferably be provided that the casting mold wall has a height of at least 10 mm.

The at least one opening is preferably arranged only in the shaping surface of the casting mold upper part. In this way, low-viscosity bone cements can also be introduced into the cavity without being able to flow out through the at least one opening in the cavity.

The shaping surface of the casting mold upper part may likewise be shaped as a cavity.

The casting mold wall preferably encloses an interior which adjoins the volume delimited by the cavity of the casting mold lower part.

The container may be open but is preferably impermeably closed or closable for bone cement paste in order to prevent contamination of the surroundings by the bone cement paste.

For producing hip and shoulder spacers, the casting mold is preferably divided into the casting mold lower part and the casting mold upper part in the middle of the spacer to be produced. This means that one spacer half is shaped by the cavity of the casting mold lower part and the second spacer half by the shaping surface of the casting mold upper part.

In the case of the tibial and also the femoral component of knee spacers, it is advantageous and preferred for the cavity of the casting mold lower part to reproduce the shape of the sliding surfaces and the shaping surface of the casting mold upper part to reproduce the respective back face of the knee spacer component. In this case, the divide is advantageously located at the upper edge of the rear sides of the knee spacer components.

The device is preferably suitable for low-viscosity bone cement paste or for cooled medium- to high-viscosity bone cement paste.

The at least one container for receiving bone cement paste is preferably impermeably closed to the outside for the bone cement paste.

The cavity is preferably shaped in the manner of a hemispherical shell.

In the device according to the invention, it may be provided that mutually opposing parts of the casting mold wall are oriented parallel to one another or the casting mold wall tapers slightly conically in the direction of the cavity or the casting mold wall has the shape of a right or skewed general cylinder, the base area of which is delimited by the peripheral edge of the cavity.

In this way, the casting mold upper part can be linearly displaced in the casting mold wall and, apart from the at least one opening, simultaneously seal the hollow space at the top. As a result, the bone cement paste in the casting mold can be pressed into the desired shape.

The casting mold tapering slightly conically in the direction of the cavity means that the acute angle of the cone or the angle at which walls are inclined towards one another amounts to no more than 15°, preferably no more than 4° and particularly preferably no more than 1°.

A general cylinder is obtained by linear displacement of a base area, in this case the base area which is delimited by the peripheral edge of the cavity. In a right cylinder, displacement proceeds perpendicularly to this base area while in a skewed cylinder it proceeds at an angle other than 90°.

Provision may moreover be made for an internal wall to extend peripherally from a peripheral edge of the shaping surface of the casting mold upper part away from the cavity of the casting mold lower part, wherein the internal wall preferably at least in places delimits the at least one container and/or mutually opposing parts of the internal wall are oriented parallel to one another or the internal wall has the shape of a right or skewed general cylinder, the base area of which is delimited by the peripheral edge of the shaping surface of the casting mold upper part.

The internal wall can provide a flat seal against the casting mold wall. At the same time, the casting mold upper part is stably guided in the casting mold wall.

The internal wall is denoted as such because it is arranged on the inside relative to the casting mold wall. In the present case, an internal wall should not in any event be taken to mean an inwardly oriented side of a wall but instead a physical wall with a volume.

The internal wall may preferably be embodied in one-piece with the casting mold upper part and particularly preferably be part of the casting mold upper part.

Provision may also be made for the internal wall to have height of at least 10 mm.

Provision may moreover be made for the outer circumference of the internal wall to be exactly the same size as or slightly smaller than the inner circumference of the casting mold wall.

Provision may also be made for the internal wall and the casting mold wall to rest flush against one another when the casting mold upper part is pushed into the casting mold wall and/or the internal wall forms a seal against the casting mold wall for the bone cement paste when the casting mold upper part is pushed into the casting mold wall.

In this way, a hollow space sealed to the outside for forming the spacer is formed in the interior of the assembled casting mold parts of the device. In addition, tilting of the casting mold upper part relative to the casting mold lower part is prevented in this way. It is thus possible to prevent the surfaces of the spacer being unintentionally inclined towards one another, for example the tibial plateau being unintentionally tilted relative to a residual tibial knee spacer component. Furthermore, the punch-like casting mold upper part is in this way stabilized, such that the casting mold upper part can also be fabricated from thin plastics films.

It is provided that the device has one or two lid(s) with which the casting mold upper part is closed or closable to the outside on the side opposite from the shaping surface of the casting mold upper part, such that an upper container closed to the outside is formed as one of the at least one containers for receiving bone cement paste between the casting mold upper part and the lid and/or with which the casting mold lower part is closed or closable to the outside on the side opposite from the cavity of the casting mold lower part, such that a lower container closed to the outside is formed as one of the at least one containers for receiving bone cement paste between the casting mold lower part and the lid.

It is here provided that the or one of the lid(s) is placed or placeable into or onto the casting mold upper part or into or onto the internal wall of the casting mold upper part in order to close the side opposite from the shaping surface of the casting mold upper part to the outside and there form a closed container for receiving excess bone cement paste, and/or the or one of the lid(s) is placed or placeable into or onto the casting mold lower part in order to close the side opposite from the cavity of the casting mold lower part to the outside and there forms a closed container for receiving excess bone cement paste.

The lid(s) mechanically stabilize(s) the casting mold upper part and/or the casting mold lower part, in particular if the casting mold upper part and the casting mold lower part are produced from or with plastics films. This further prevents any bone cement paste emerging from the at least one opening from contaminating or soiling the surroundings. In this way, the user is protected from any possibly harmful contact with the bone cement paste and contamination of the spacer through the at least one opening is prevented or at least made more difficult.

A further development of the present invention may provide that the lid or lids has at least one vent opening and/or the lid or lids are gas-permeably closed or closable with the casting mold upper part.

In this way, air can escape from the upper or lower container delimited with the lid or the containers delimited with the lids when the bone cement paste flows through the at least one opening in the container(s). Any possible build-up of gas back-pressure can thereby be prevented.

Provision may moreover be made for the volume of the cavity of the casting mold lower part and the volume delimited by the casting mold wall together to be larger than the volume of the spacer to be produced.

This ensures that the bone cement paste can be introduced in excess in order to avoid entrapped air in the spacer.

Provision may also be provided for the casting mold wall and the casting mold lower part to be formed as one part, wherein the casting mold wall is preferably part of the casting mold lower part.

In this way, the device is less costly and simpler to produce.

Provision may also be made for the device to have a mixing system for mixing bone cement paste, a cement powder and a monomer liquid, wherein the cement powder and the monomer liquid are stored separately from one another, wherein the bone cement paste is mixable from the cement powder and the monomer liquid with the assistance of the mixing system.

Provision may here also preferably be made for the mixing system to include a mixing cup which preferably has a spout for introducing the bone cement paste from the mixing cup into the cavity and the interior delimited by the casting mold wall. Provision may alternatively be made for the mixing system to be a bone cement cartridge for storing and mixing the cement powder and the monomer liquid and for delivering mixed bone cement paste from the bone cement cartridge, wherein the bone cement cartridge preferably contains the cement powder and the monomer liquid in regions separated from one another in liquid-tight manner.

The mixing system further completes the device and can be used directly for producing the spacer.

Theoretically, the device may also only include the cement powder and the monomer liquid, preferably a closed first container containing the cement powder and a closed second container containing the monomer liquid.

Provision may further be made for the casting mold lower part and the casting mold upper part, and preferably also the casting mold wall and if present the lid or lids to consist of a plastics film or substantially consist of a plastics film or the casting mold lower part and the casting mold upper part, and preferably also the casting mold wall and if present the lid or lids in each case to be composed of two or more plastics films which are connected together and particularly preferably welded or adhesively bonded together.

In this way, the structure is particularly inexpensive but at the same time surprisingly still sufficiently robust to mold the bone cement spacer therein. In addition, after use, the device can thus be inexpensively and hygienically disposed of by incineration.

The casting mold lower part and the casting mold upper part, and if present the casting mold wall and/or the lid substantially consisting of a plastics film or of two or more joined together plastics films means that at least 50% of the volume or weight of the casting mold lower part and the casting mold upper part, and optionally of the casting mold wall and/or the lid, consists of the plastics film or of the two or more joined together plastics films.

The casting mold lower part and the casting mold upper part, and preferably also the casting mold wall and if present the lid or lids, may preferably be produced by thermoforming plastics films.

For the purposes of the present patent application, a film should preferably have a thickness of a maximum of 2 mm and preferably a thickness of a maximum of 1 mm.

The film or joined together films should preferably be self-supporting, i.e. not assume the form of a coating.

Provision may also preferably be made for the casting mold lower part, the casting mold upper part and the casting mold wall and if present the lid or lids substantially or entirely to consist of a plastics material and preferably to be fabricated from a polyolefin, polyethylene (PE) or polypropylene (PP) and particularly preferably from a PETG film and/or a polyamide film and/or a PE film.

In this way too, the structure is particularly inexpensive. In addition, after use, the device can thus be inexpensively and hygienically disposed of by incineration.

Provision may be made for the at least one opening to have a minimum cross-sectional length of a maximum of 2.5 mm, preferably a minimum cross-sectional length of a maximum of 2 mm, particularly preferably a minimum cross-sectional length of a maximum of 1.5 mm and very particularly preferably a minimum cross-sectional length of a maximum of 1 mm.

The maximum cross-sectional lengths ensure that the bone cement paste cured in the at least one opening, i.e. the sprue formed in the at least one opening, can still be sheared off or broken off without a tool in order to demold the spacers. Once the cement paste has cured, the small diameter of the at least one opening means that the bone cement sprues passing therethrough, which connect the cured spacers with the excess bone cement paste on the side opposite from the shaping surface of the casting mold upper part, can readily be detached by shearing or breaking.

The minimum cross-sectional length of an opening is taken to mean the narrowest dimension of the cross-sectional area suitable for free flow (perpendicular to the direction of flow). In the case of a slit-shaped opening, this is for example the width and not, for instance, the length of the slit.

Provision may moreover be made for the at least one opening to have a minimum cross-sectional length of at least 0.2 mm, preferably of at least 0.5 mm and particularly preferably of at least 1 mm.

The minimum cross-sectional lengths ensure that the bone cement paste can be pressed without excessively high mechanical pressure through the at least one opening, even if the bone cement paste has an elevated viscosity. The excess bone cement paste can flow unproblematically through openings dimensioned in this way without there being any need to exert any excessive pressure on the bone cement paste which either cannot be applied manually or might destroy or damage the casting mold.

The at least one opening is preferably not slit-shaped and is particularly preferably at most twice as long as it is wide.

A further development may provide that at the end of the casting mold wall opposite from the cavity of the casting mold lower part, a limit stop is arranged for limiting the movement of the casting mold upper part within the casting mold wall in the direction of the cavity, wherein a contact surface is preferably arranged as a limit stop at the end of the casting mold wall opposite from the cavity of the casting mold lower part, which contact surface particularly preferably projects out at right angles from the casting mold wall.

In this way, the casting mold upper part can be pushed into the casting mold wall until the limit stop is reached in order to mold the spacers from the bone cement paste.

Provision may also be made for the device to have a metal core which is to be or is arranged in the cavity, wherein the device preferably has a plurality of spacing pieces which keep the metal core in the cavity spaced from the internal side of the cavity and from the internal side of the casting mold wall, wherein the spacing pieces particularly preferably consist of cured bone cement and in particular of polymethyl methacrylate (PMMA).

In this way, a mechanically stabilizing reinforcement in the form of the metal core can be arranged in the spacer which is to be produced.

In devices with a metal core provision may be made for the metal core to have bores for receiving pin-shaped spacing pieces, wherein the bores are preferably not arranged in a region of the cavity for molding a sliding surface of the spacer and particularly preferably the bores are arranged in a region of the cavity for molding a stem of the spacer.

It is advantageous for producing hip and shoulder spacers for a metal core to be arranged in the casting mold lower part, which metal core is spaced from the wall of the casting mold lower part by spacing pieces. Pins of polymethyl methacrylate are particularly suitable as spacing pieces. These pins bond with the bone cement paste and, after curing, can be trimmed to the contour of the spacer.

Provision may moreover be made for the casting mold lower part or the casting mold lower part and the casting mold wall or the casting mold lower part, the casting mold wall and the casting mold upper part to be transparent or translucent.

In this way, it is possible during filling of the cavity and also during forming of the spacer to monitor visually whether and how the spacer mold is filling with the bone cement paste and how it is curing therein. It is thus possible to monitor visually whether the spacer is obtaining the desired shape.

Provision may further be made for the at least one opening to be arranged in the regions which, in the normal disposition of the casting mold, are the highest points of the hollow space.

In this way, it is possible to prevent entrapped air which cannot escape from the hollow space from forming in the hollow space.

Provision may also be made for the shaping surface of the casting mold upper part to rest with an outer edge internally against the casting mold wall and, when the casting mold upper part is pushed in, for the edge to slide internally on the casting mold wall, wherein the edge preferably has a wiper rim or wiper lip.

This ensures that, when the casting mold upper part is pushed in to collect and compress the bone cement paste, the bone cement paste can be used in the interior of the casting mold.

Provision may moreover be made for the device to have a stand, wherein the casting mold lower part is insertable into the stand and the stand is suitable, with the casting mold lower part therein, to be placed on a flat support, wherein the stand preferably substantially or entirely consists of a plastics film or of two or more plastics films which are joined together and are particularly preferably welded or adhesively bonded together.

This has the advantage that, during shaping of the spacer, the device can be placed on a flat support, such as a table. At the same time, the stand can be used for stabilizing the casting mold, in particular the casting mold lower part.

The stand may substantially or entirely consist of PE, PP, or polyolefin.

The stand substantially consisting of a plastics film or of two or more joined together plastics films means that at least 50% of the volume or weight of the stand consists of the plastics film or of the two or more joined together plastics films.

The objects underlying the present invention are also achieved by a method for producing a spacer for temporarily replacing a joint or part of a joint, in particular a hip joint, a knee joint or a shoulder joint, comprising an articulating surface of the joint, wherein the method is carried out with an above-stated device, the method having the following chronological steps:

A) introduction of flowable bone cement paste into the cavity and the interior delimited by the casting mold wall, wherein a larger volume of the flowable bone cement paste is introduced than is required by the spacer;

B) insertion of the casting mold upper part into the casting mold wall, wherein the shaping surface points in the direction of the cavity;

C) pushing in of the casting mold upper part in the direction of the cavity within the casting mold wall;

D) emergence of excess bone cement paste through the at least one opening as the casting mold upper part continues to be pushed in, wherein the excess bone cement paste flows into the at least one container for receiving the excess bone cement paste;

E) completion of pushing in when a limit stop is reached or when a desired height of the spacer is reached;

F) curing of the bone cement paste in the hollow space formed by the cavity, the shaping surface of the casting mold upper part and the casting mold wall; and G) removal of the spacer molded and cured in this manner from the hollow space, wherein sprues of the cured bone cement paste formed in the at least one opening are detached.

The method is preferably carried out with PMMA bone cement paste.

The method is preferably applied with low-viscosity bone cement paste or with cooled medium-to high-viscosity bone cement paste.

Provision may also be made in step D) for the excess bone cement paste to flow into a lower container closed by a lid for receiving the excess bone cement paste on the casting mold lower part and be enclosed therein and/or to flow into an upper container closed by a lid for receiving the excess bone cement paste on the casting mold upper part and be enclosed therein, wherein, on demolding the cured spacer after step F) or in step G), the cured excess bone cement paste remains in the lower container and/or the upper container.

This prevents the bone cement paste from getting out and contaminating the surroundings.

Provision may moreover be made before step A) for the bone cement paste to be mixed from a monomer liquid and a cement powder, in particular until a homogeneous bone cement paste is obtained, and, preferably before step A), for a metal core to be arranged in the cavity, wherein the metal core is particularly preferably spaced from the internal side of the cavity and the casting mold wall with the assistance of pin-shaped spacing pieces.

This completes the method.

Provision may also be made during step C) for the air to be expelled through the at least one opening from the hollow space delimited by the cavity of the casting mold lower part, the shaping surface of the casting mold upper part and the casting mold wall.

This prevents unintended defects from being formed in the spacer by entrapped air.

Provision may finally be made after step F) and before step G) for the casting mold upper part to be withdrawn from the open end of the casting mold wall.

This simplifies demolding of the spacer.

The invention is based on the surprising recognition that it is possible by pushing two parts of a casting mold into one another, the casting mold containing an excess of bone cement paste to produce a spacer, by means of a very highly simplified and inexpensive casting mold the excess bone cement paste being able to emerge from the casting mold through at least one suitable opening in the shaping surfaces. The emerging bone cement paste is preferably captured and enclosed in closed regions on the casting mold. The at least one opening is preferably arranged at a point of the casting mold which is arranged at the top during use of the casting mold in order to enable entrapped air to emerge through the at least one opening and so avoid defects in the spacer. The at least one container for receiving excess bone cement paste prevents the user and the surroundings from being contaminated with bone cement paste emerging from the casting mold when the device is being used. At the same time, use of the device is simplified as a result.

An exemplary device according to the invention may be composed of a) a casting mold lower part which contains on the top thereof at least one cavity for shaping the spacer, b) a casting mold wall arranged vertically and upwardly adjoining the cavity, wherein mutually opposing wall parts of the casting mold wall are parallel to one another, wherein the peripheral casting mold wall encloses an interior, c) a casting mold upper part which contains on the bottom thereof at least one surface for shaping the spacer, d) an internal wall arranged vertically and upwardly adjoining the shaping surface, wherein mutually opposing wall parts of the internal wall are parallel to one another, e) a lid which is inserted into the casting mold upper part and closes the space formed by the top of the casting mold upper part and the internal wall as a container for receiving excess bone cement paste, f) at least one opening in the wall of the casting mold upper part which connects the shaping surface of the casting mold upper part with the space formed by the top of the casting mold upper part and the internal wall, g) wherein the casting mold upper part is arranged vertically slidably in the casting mold lower part, h) wherein the sum of the volumes of the cavity and of the interior delimited by the circumferential casting mold wall is larger than the volume of the spacer to be produced, and i) wherein once the cavity and the interior delimited by the circumferential casting mold wall have been filled with bone cement paste and the casting mold upper part has subsequently been pushed in the direction of the cavity, the excess bone cement paste emerges through the at least one opening in the container for receiving excess bone cement paste, which is closed at the top by the lid, and remains therein.

The device according to the invention is used in such a manner that firstly bone cement paste is introduced into the cavity of the casting mold lower part and the interior delimited by the casting mold wall. The volume of the bone cement paste should be somewhat larger than the volume of the spacer to be produced. The casting mold upper part is then inserted into the casting mold lower part. The outside of the internal wall of the casting mold upper part rests internally against the casting mold wall of the casting mold lower part. Pressure is then applied to the casting mold upper part or the lid of the casting mold upper part and the casting mold upper part is moved downwards in the direction of the cavity of the casting mold lower part. The air located above the bone cement paste in the interior delimited by the casting mold wall and the shaping surface of the casting mold upper part escapes through the at least one opening in the space formed by the top of the casting mold upper part and the internal wall, i.e. into the container for receiving excess bone cement paste. The bone cement paste comes into contact with and then covers the shaping surface of the casting mold upper part. As movement continues, the bone cement paste flows along the contour of the wall of the cavity (the internal side of the cavity) of the casting mold lower part until the bone cement paste has reached the at least one opening. The cavity of the casting mold lower part and the shaping surface of the casting mold upper part are thus filled with bone cement paste. The spacer is shaped as a result. The bone cement paste then cures by free-radical polymerization. Once curing is complete, the casting mold upper part is withdrawn from the casting mold lower part. The formed spacer usually remains stuck to the casting mold upper part since it is connected to the casting mold upper part by undercuts in the region of the at least one opening. The casting mold upper part is then detached from the spacer. In so doing, bone cement sprues which lead through the at least one opening are sheared off and remain in the container for receiving excess bone cement paste.

An exemplary method according to the invention for producing spacers with the device according to the invention may comprise the following successive steps:

a) mixing a cement powder with a monomer liquid and homogenizing the cement components until a homogeneous bone cement paste is obtained,
b) introducing the bone cement paste into the cavity of the casting mold lower part and the interior delimited by the casting mold wall,
c) inserting the casting mold upper part into the interior delimited by the casting mold wall of the casting mold lower part,
d) pressing the casting mold upper part down in the direction of the cavity of the casting mold lower part,
e) expelling the air through the at least one opening from the interior of the casting mold between the bone cement paste and the shaping surface of the casting mold upper part into the space formed by the top of the casting mold upper part and the internal wall,
f) expelling the excess bone cement paste from the interior of the casting mold through the at least one opening into the space formed by the top of the casting mold upper part and the internal wall as a container for receiving excess bone cement paste,
g) curing the bone cement paste,
h) withdrawing the casting mold upper part and
i) demolding the cured spacer, wherein the cured excess bone cement paste remains in the space formed by the top of the casting mold upper part and the internal wall as a container for receiving excess bone cement paste.

Further exemplary embodiments of the invention are explained below with reference to thirty-five schematic figures but without thereby limiting the invention. In the figures:

FIGS. 1 to 9 are drawings showing various views of a first exemplary embodiment of a device according to the invention for producing a spacer for a hip joint and parts of the device. FIGS. 1 to 11 show the course of a first exemplary embodiment of a method according to the invention which is carried out using the device according to the first exemplary embodiment.

Figure 8:
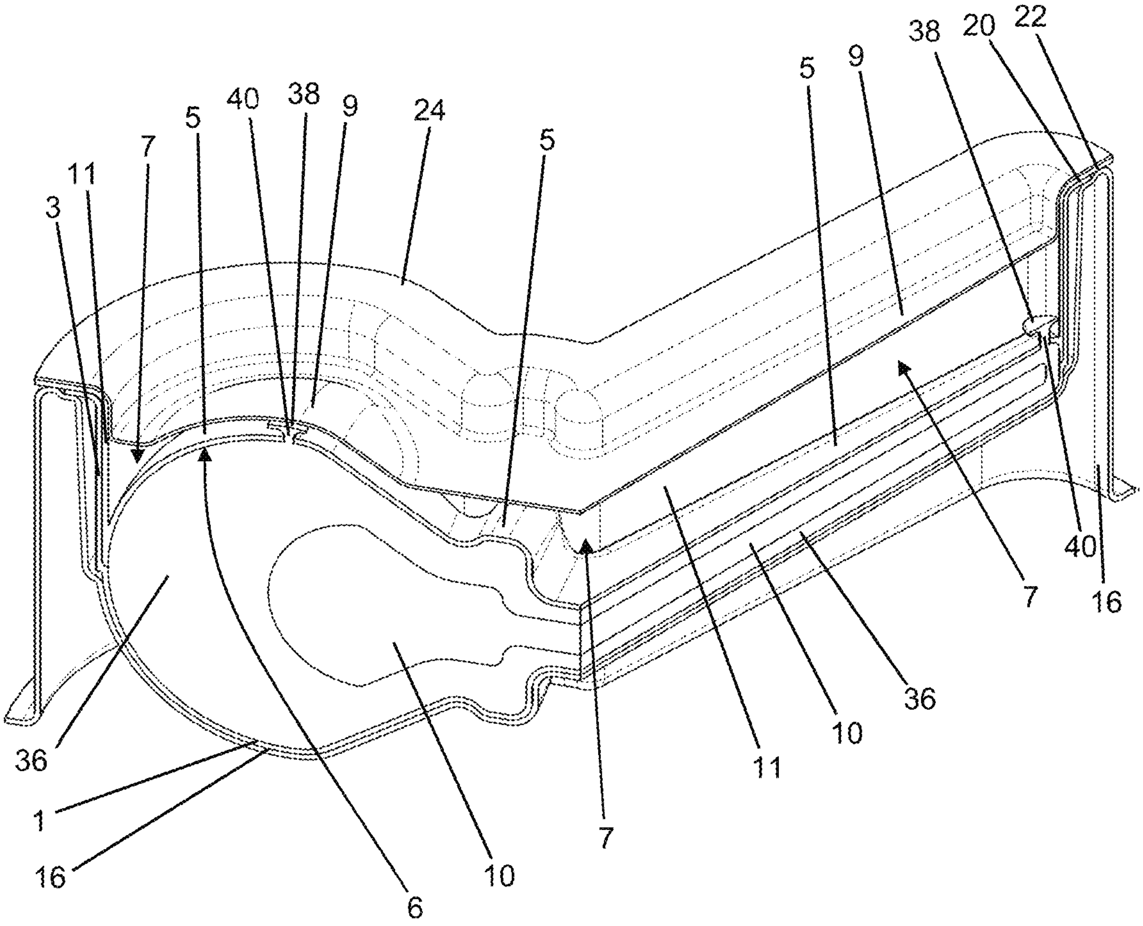
FIG. 8 shows a schematic perspective angled cross-sectional view onto the casting mold filled with bone cement paste of the first exemplary embodiment in the closed state.

The first device according to the invention is suitable and provided for producing a spacer 42 (see FIGS. 10 and 11) for a hip joint. The device comprises a multipart casting mold. The casting mold has a casting mold lower part 1 and a casting mold upper part 5. A cavity 2 for receiving bone cement paste 36 (see FIGS. 4, 5 and 8) and for forming part of the surface of the spacer 42 to be produced is arranged in the casting mold lower part 1. The cavity 2 can shape one half of the spacer 42. A casting mold wall 3, which extends the hollow space formed by the cavity 2 with an interior 4, may be arranged at the edge of the cavity 2. The casting mold wall 3 may to this end peripherally enclose the edge of the cavity 2. The walls of the casting mold wall 3 may be oriented parallel to one another, such that the casting mold wall 3 has a generally cylindrical geometry, wherein the base area of the general cylinder is defined by the area which delimits the edge of the cavity 2. The interior 4 for introduction of bone cement paste 36 is arranged within the walls of the casting mold wall 3, which interior is connected, and preferably also aligned, with the cavity 2.

The casting mold upper part 5 may preferably be inserted or pushed into the casting mold lower part 1. The casting mold upper part 5 has at the bottom thereof a shaping surface 6, with which a further part of the surface of the spacer 42 to be produced is shapeable and preferably the remaining part of the surface of the spacer 42 to be produced is shapeable. Together with the cavity 2, the shaping surface 6 may define the entire surface of the spacer 42 or at least 90% of the entire surface of the spacer 42. The shaping surface 6 may form an indentation in the casting mold upper part 5. It is also possible for part of the casting mold wall 3 to form part of the surface of the spacer 42 or for one or more inserts (not shown), which shape part of the surface of the spacer 42, additionally to be inserted into the cavity 2 and/or placed on the shaping surface 6.

Figure 9:
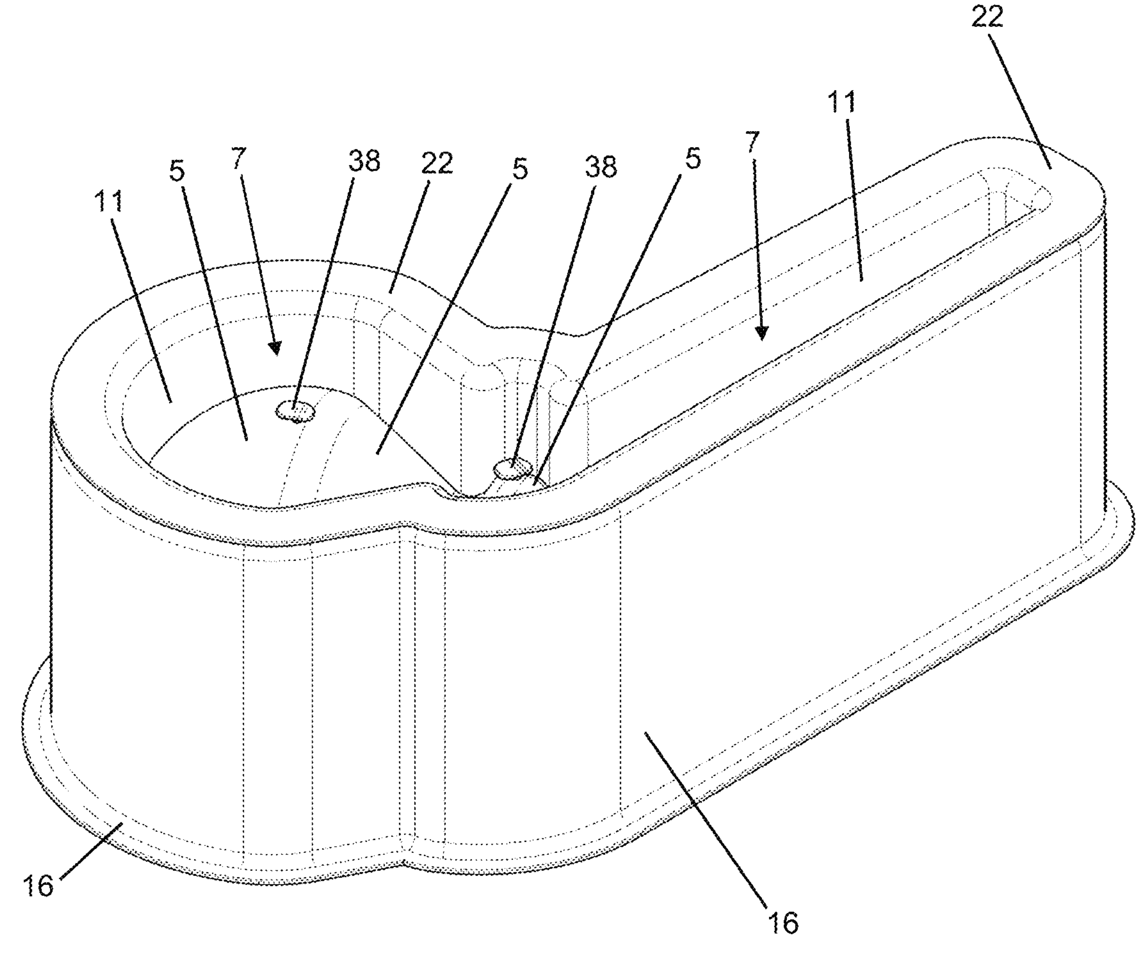
FIG. 9 shows a schematic perspective view onto the device according to FIG. 8 without lid.

A container 7 for receiving excess bone cement paste 38 (see FIGS. 8 and 9) may be arranged on the side of the casting mold upper part 5 opposite from the shaping surface 6. Openings 8, which provide a through-connection for the excess bone cement paste 38 from the side of the shaping surface 6 to the container 7, may be present in the shaping surface 6. The openings 8 are preferably arranged at the points of the shaping surface 6 which, in the proper disposition of the device, are the highest shaping points of the casting mold. In this way, gases entrapped in the casting mold may escape through the openings 8 such that entrapped air is avoided in the spacer 42 to be produced.

The container 7 may have been or be impermeably closed to the outside for the bone cement paste 36 with a lid 9. An internal wall 11, which delimits the container 7, may start from and extend away from the back face of the shaping surface 6. The internal wall 11 may align externally with a perfect fit with the casting mold wall 3. In this way, the casting mold upper part 5 can be inserted with a perfect fit into the casting mold wall 3 of the casting mold lower part 1 and the bone cement paste 36 accordingly collected from the inside of the casting mold wall 3 and pressed into the cavity 2 and the shaping surface 6. It may also be sufficient to this end if the casting mold wall 3 tapers in the direction of the cavity 2, wherein the taper must to this end have an acute angle.

The container 7 may be gas-permeably connected with the surroundings. Provision may be made to this end for the lid 9 not to close pressure-tightly and/or for small vent openings (not visible in the figures) to be arranged in the lid and/or the internal wall 11.

A metal core 10 may be provided as reinforcement for the spacer 42. The metal core 10 may to this end be held spaced from the internal side of the cavity 2 and from the casting mold wall 3 with the assistance of pin-shaped spacing pieces 12 of cured PMMA, such that the bone cement paste 36 can flow completely around the metal core 10 between the metal core 10 on the one hand and the internal side of the cavity 2 and the shaping surface 6 on the other. In order to position the spacing pieces 12, bores 14 may be provided in the metal core 10 for receiving one end of the pin-shaped spacing pieces 12. Matching indentations for receiving the opposite end of the pin-shaped spacing pieces 12 may likewise be arranged in the internal side of the cavity 2.

A stand 16, into which the casting mold lower part 1 may be placed or inserted, may be provided in order to position the casting mold correctly with the casting mold lower part 1 underneath and the casting mold wall 3 perpendicularly on top. The stand 16 may be provided for placement on a flat surface such as a table.

The casting mold lower part 1, the casting mold upper part 5, the lid 9 and the stand 16 may be inexpensively produced from a plastics film or a plurality of joined together plastics films, in particular by injection molding or by thermoforming. In the assembled state, the parts of the device produced from the plastics films stabilize one another mechanically. The plastics film(s) preferably consist of a polyolefin, a polyethylene (PET) or a glycol-modified PET (PETG).

When a plurality of films are used, they may be laminated together with an adhesive or by elevated temperature.

Internally located grooves 18 and externally located sprues 19, which extend from a limit stop 20 on the side of the casting mold wall 3 opposite from the cavity 2 down to the edge of the cavity 2, may be arranged in the casting mold wall 3. The sprues 19 may contain the volume for forming the grooves 18. The ends of the pin-shaped spacing pieces 12, which have been inserted into the bores 14 of the metal core 10 and project out therefrom, may be guided to the cavity 2 along these grooves 18.

Grooves 21 matching the sprues 19 may be provided internally in the stand 16. As a result, the casting mold lower part 1 can be pushed in guided manner into the stand 16 and the casting mold lower part 1 does not so readily become detached from the stand 16 and does not move so easily relative to the stand 16.

In order to fix the spacing pieces 12 and thus the metal core 10 in place, matching recesses 23 may be arranged at the edge of the shaping surface 6 of the casting mold upper part 5. The recesses 23 may be arranged at the edge of the shaping surface 6 in such a manner that they are moved along the grooves 18 of the casting mold wall 3 when the casting mold upper part 5 is pushed into the casting mold wall 3 of the casting mold lower part 1. The ends of the spacing pieces 12 which project out from the metal core 10 are accordingly clamped in place in the casting mold between the casting mold upper part 5 and the casting mold lower part 1.

The limit stop 20 may be arranged as a peripheral strip-shaped edge projecting out perpendicularly from the casting mold wall 3 on the side of the casting mold wall 3 remote from the cavity 2. The limit stop 20 can limit how far the casting mold upper part 5 can be pushed into the casting mold lower part 1. The casting mold upper part 5 may to this end have a mating stop 22 in the form of a peripheral edge which projects out perpendicularly from the internal wall 11 and is arranged on the side of the internal wall 11 opposite from the shaping surface 6. When the casting mold upper part 5 has been completely pushed into the casting mold lower part 1, the mating stop 22 rests against the limit stop 20. In the same way, a lid edge 24 which can be placed on the side of the mating stop 22 opposite from the limit stop 20 may be arranged on the lid 9. Because the limit stop 20, the mating stop 22 and the lid edge 24 project out from the adjoining parts at an angle, the shape of the casting mold lower part 1, the casting mold upper part 5 and the lid 9 is mechanically stabilized in the assembled state. This is in particular helpful if these parts have been fabricated from a plastics film or a plurality of plastics films by thermoforming.

The device may furthermore include a mixing cup 26 with a spout 28 for pouring bone cement paste 36 from the mixing cup 26 (see FIG. 3) and a film pouch 30 containing cement powder, an ampoule 32 containing monomer liquid and a spatula 34 for mixing the cement powder with monomer liquid in the mixing cup 26. The bone cement paste 36 may then be mixed in the mixing cup 26 before it is introduced into the casting mold or into the casting mold lower part 1. The bone cement paste 36 may, however, also be produced in another way before it is introduced into the casting mold. The device thus does not necessarily require the mixing cup 26 and also not the bone cement paste 36 or the starting components thereof. The device may in principle be applied and used with any other known system for producing a bone cement paste, such as for example with a suitable cartridge system for storing and mixing bone cement paste.

The course of a first exemplary embodiment of a method according to the invention is described below with reference to FIGS. 1 to 11.

Figure 1:
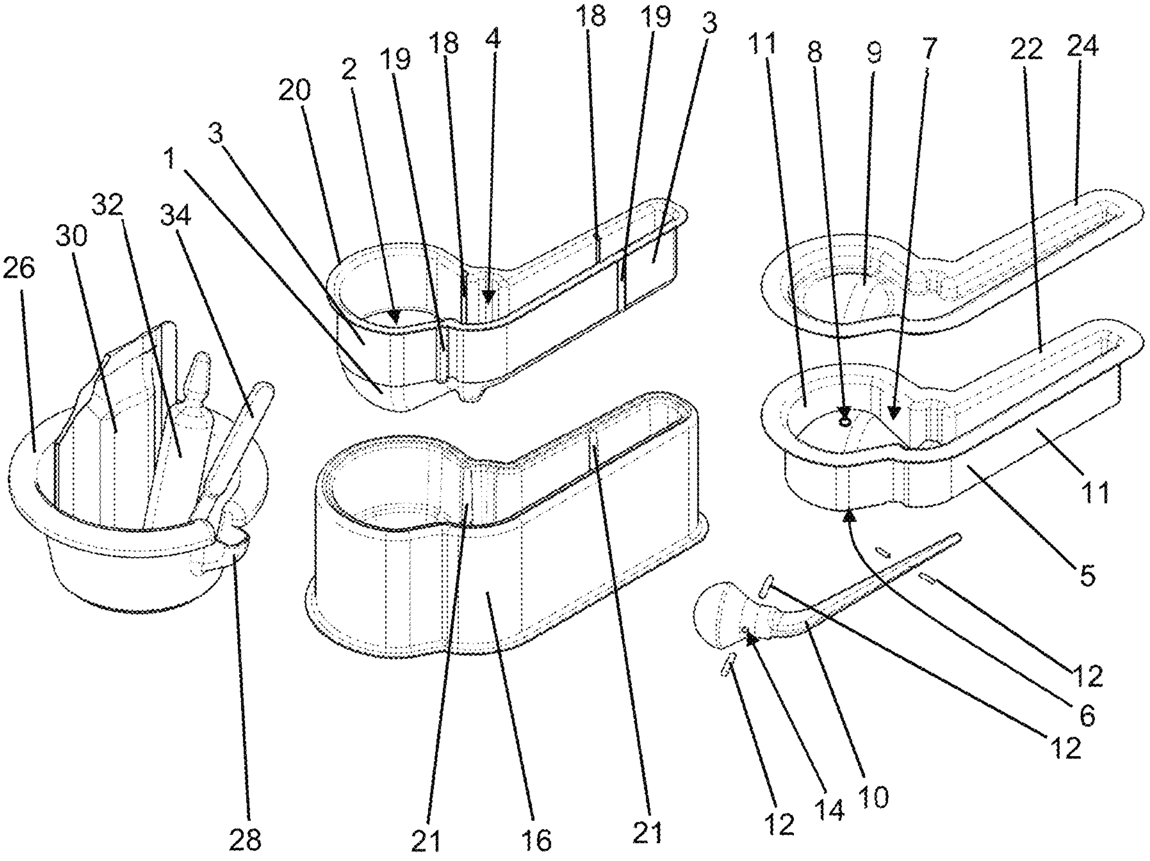
FIG. 1 shows a schematic perspective external view of a first exemplary embodiment of the present invention as a device for producing a spacer for a hip joint with separately depicted individual parts.
Figure 2:
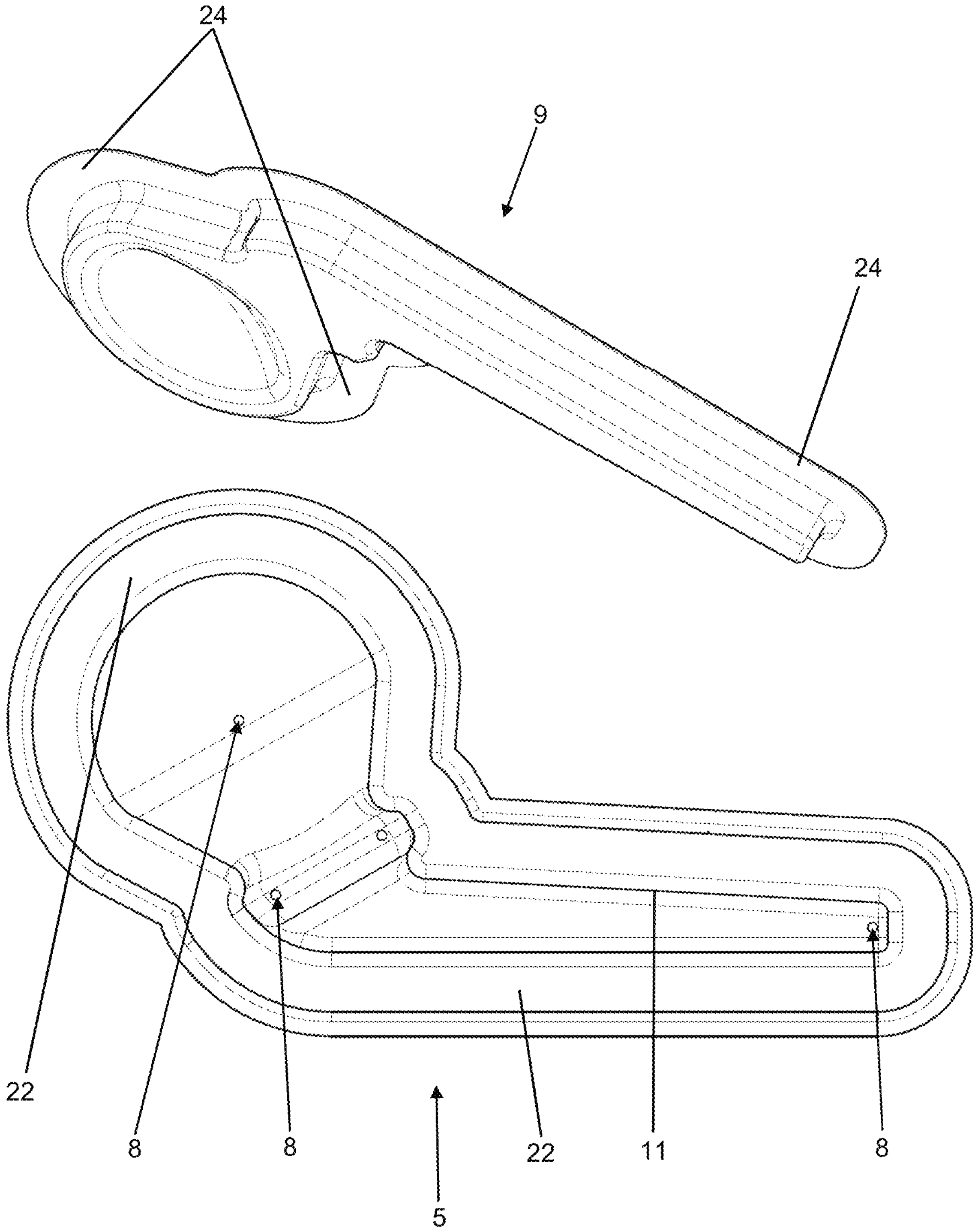
FIG. 2 shows a schematic plan view onto the open casting mold upper part.
Figure 3:
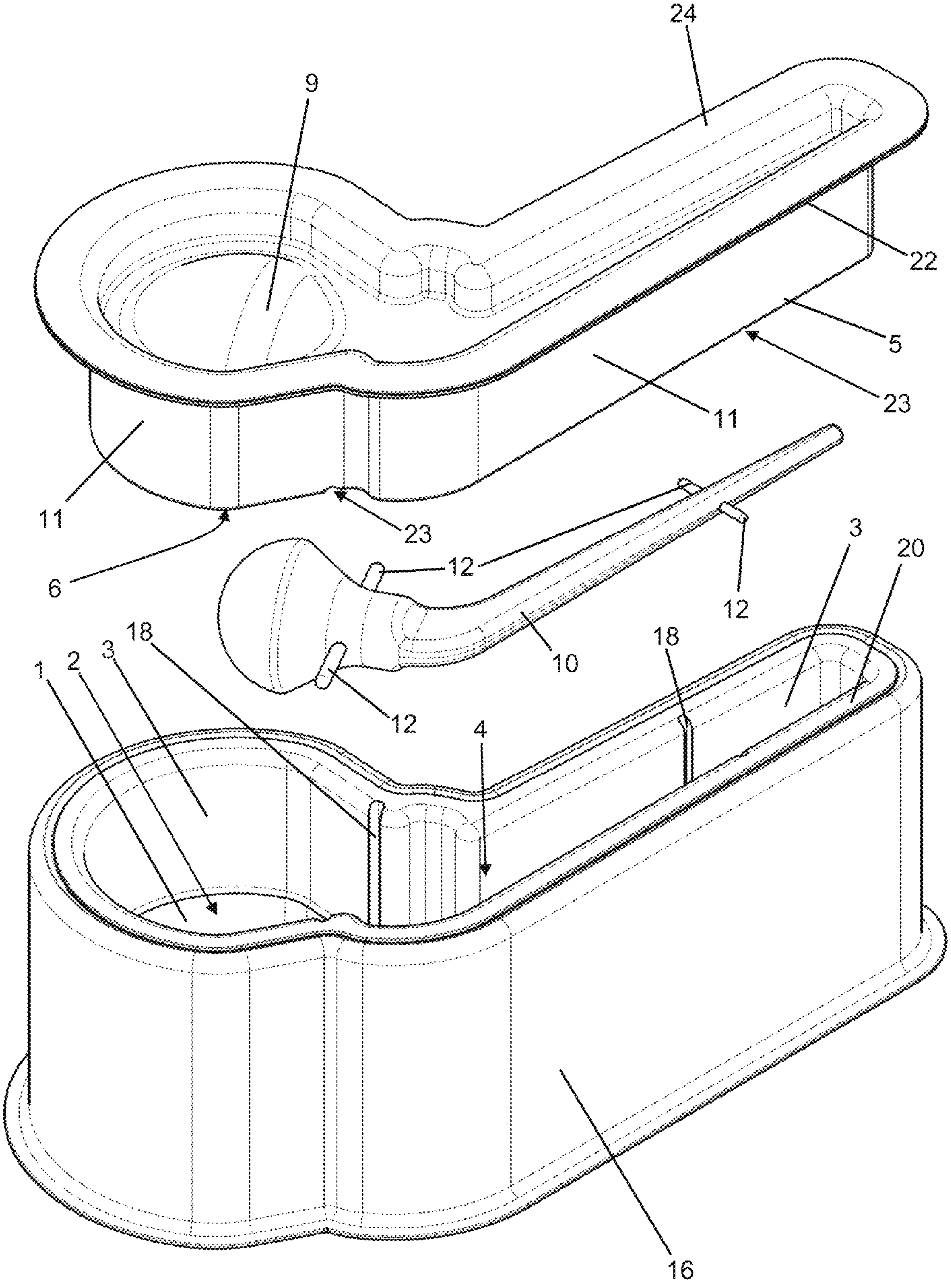
FIG. 3 shows a schematic perspective external view of the first exemplary embodiment according to FIGS. 1 and 2 prior to arrangement of the metal core in the casting mold lower part.
Figure 4:
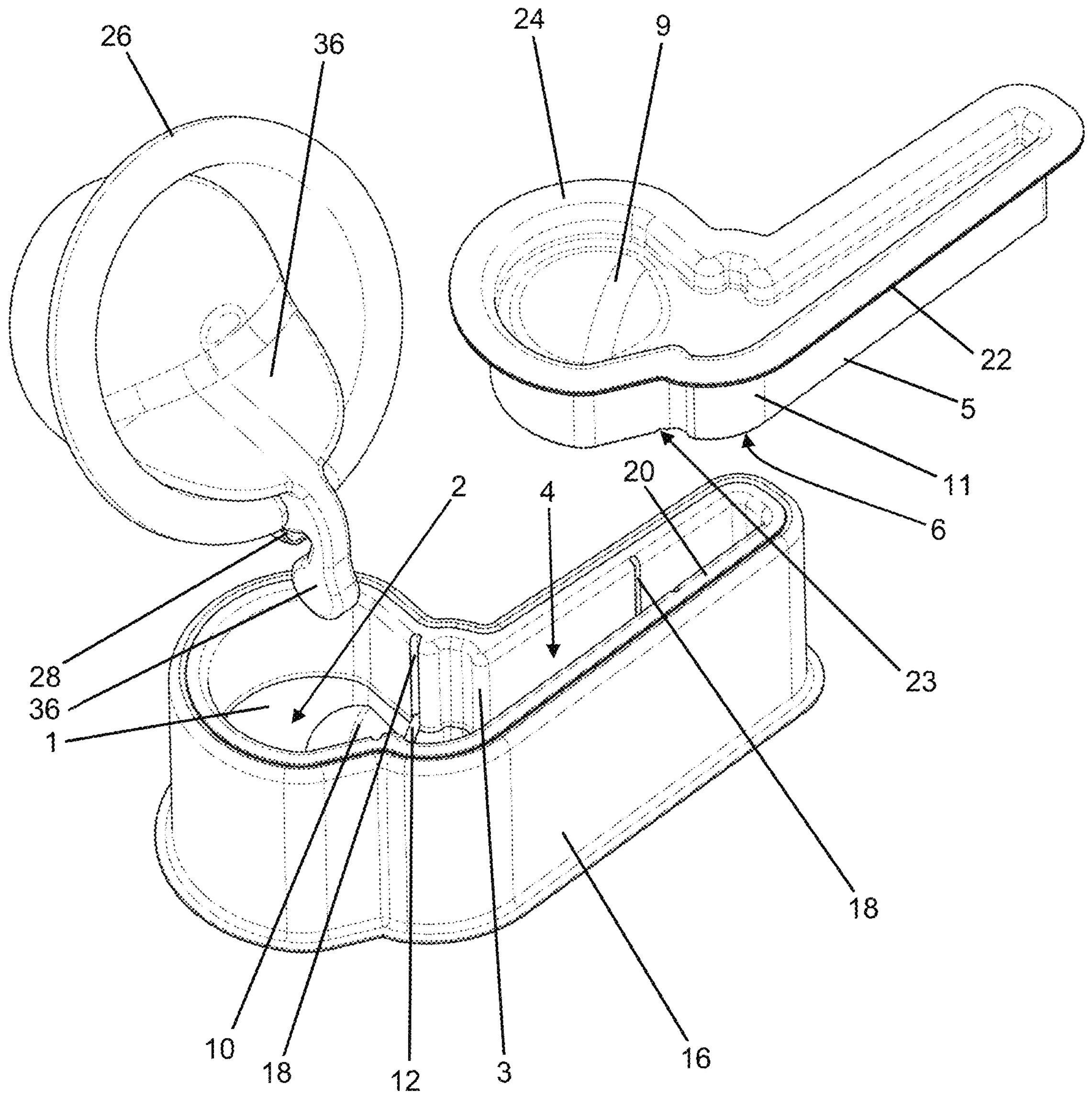
FIG. 4 shows a schematic perspective external view of the casting mold of the first exemplary embodiment during the introduction of bone cement paste.
Figure 5:
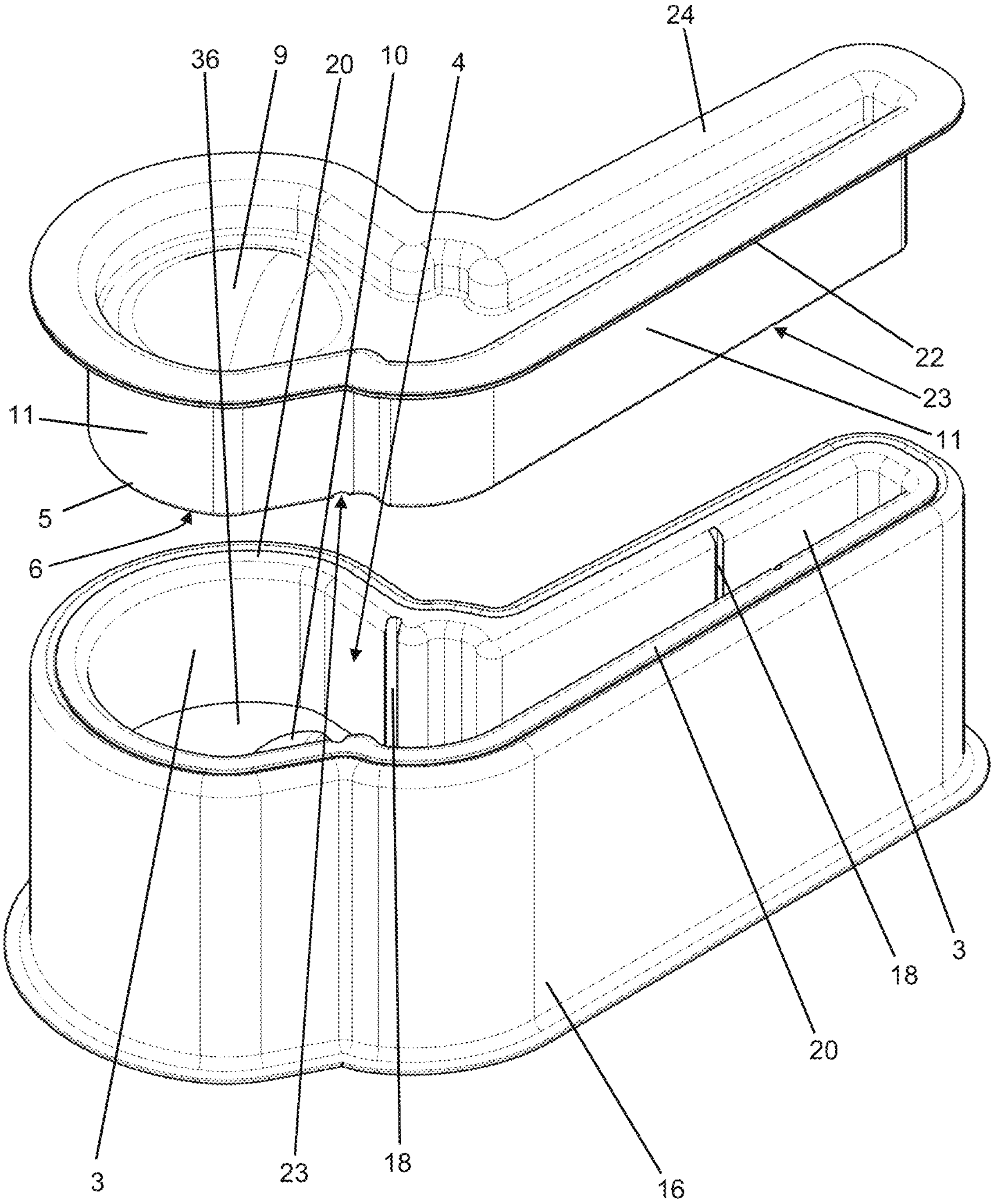
FIG. 5 shows a schematic perspective external view of the first exemplary embodiment prior to insertion of the casting mold upper part into the casting mold lower part.

The device may firstly be removed from a package (not shown) in a sterile state and may then be present as shown in FIG. 1 or in FIG. 3 or 4. If the casting mold lower part 1 has not already been inserted into the stand 16, the casting mold lower part 1 may be pushed into the stand 16 via the grooves 21. If not already present therein, the metal core 10 may be inserted into the cavity 2 (see FIG. 3). In so doing, the projecting ends of the spacing pieces 12 slide in the grooves 18 of the casting mold wall 3.

The bone cement paste 36 may be mixed by mixing the cement powder from the film pouch 30 and the monomer liquid from the ampoule 32 in the mixing cup 26 with the assistance of the spatula 34. Alternatively, the bone cement paste 36 may also be produced in any other manner.

When the metal core 10 is inserted into the cavity 2 or into the interior 4, the bone cement paste 36 can be introduced in excess into the interior 4 and the cavity 2 (see FIG. 4). The casting mold upper part 5 may then be inserted and pushed into the casting mold lower part 1 or into the casting mold wall 3. The container 7 may to this end be closed with the lid 9 (see FIG. 5).

Figure 6:
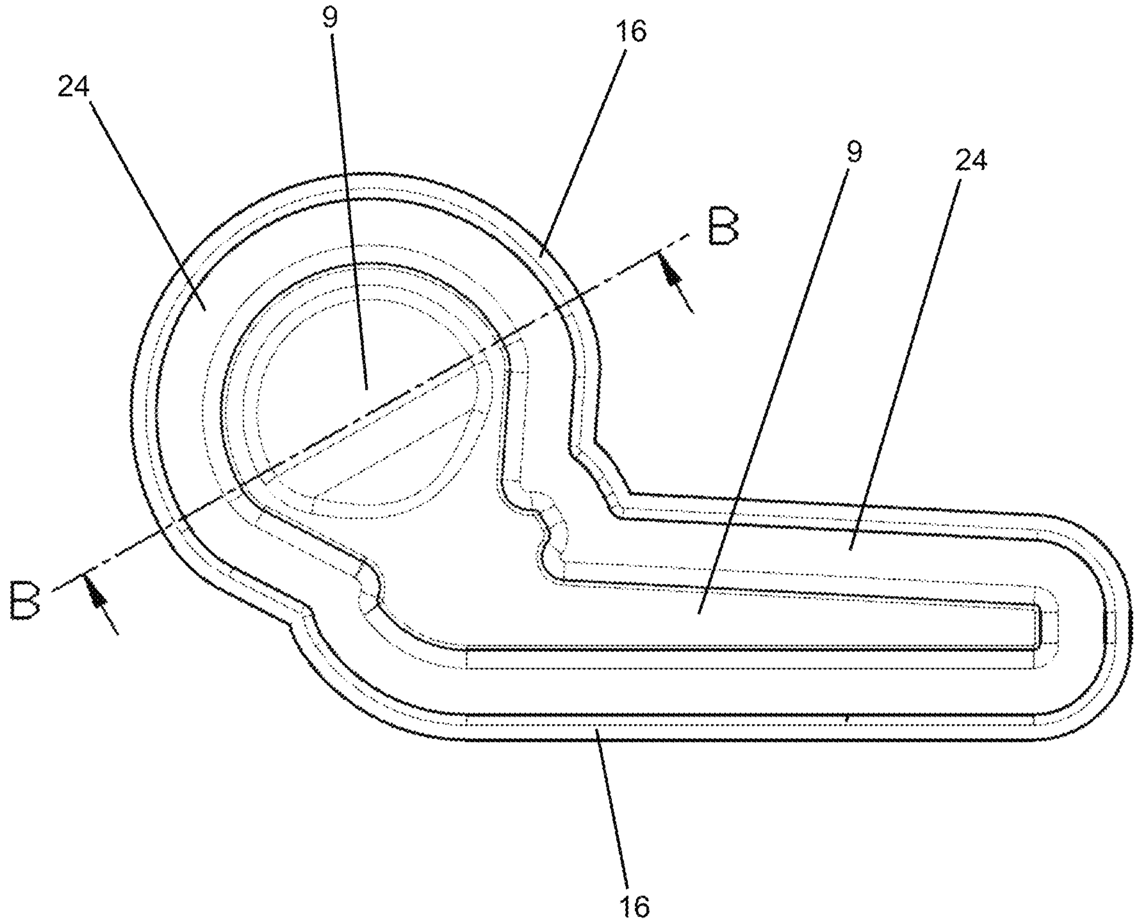
FIG. 6 shows a schematic plan view onto the closed casting mold of the first exemplary embodiment with section plane B indicated.
Figure 7:
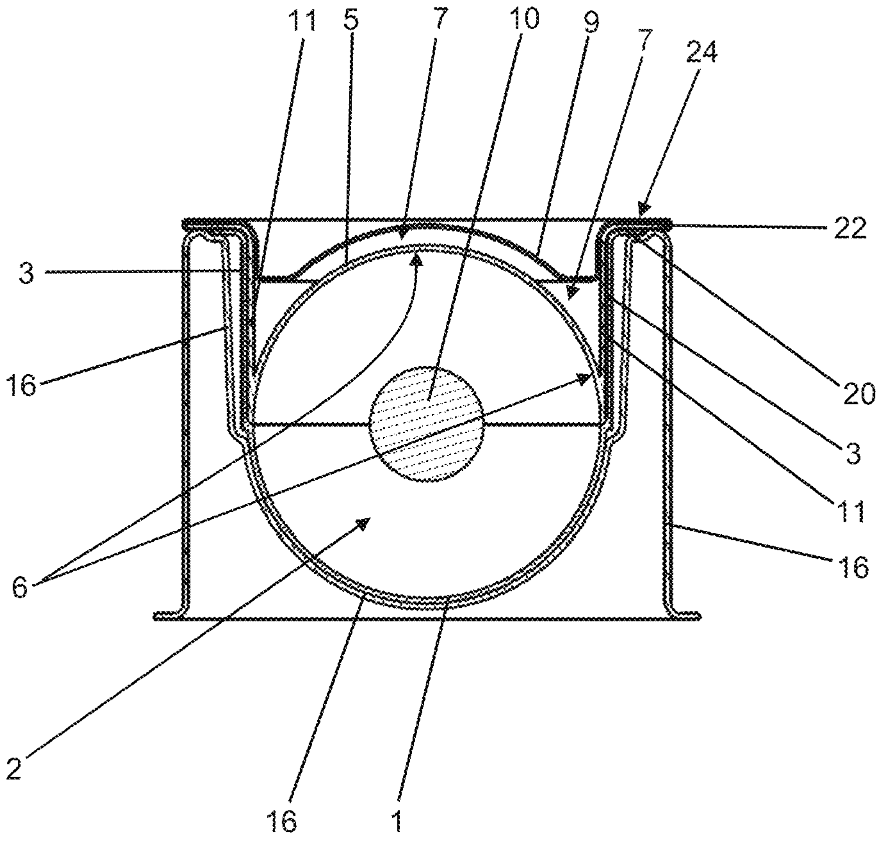
FIG. 7 shows a schematic cross-sectional view onto section B according to FIG. 6 of the first exemplary embodiment in the closed state.

The casting mold upper part 5 may be pushed into the interior 4 of the casting mold lower part 1 until the mating stop 22 rests against the limit stop 20 (see to this end FIGS. 6 and 7, which do not show the bone cement paste enclosed in the casting mold). When the casting mold upper part 5 is pushed in, the bone cement paste 36 which is present may be pressed into the cavity 2 and the volume within the casting mold continuously decreases. Excess bone cement paste 38 is pressed out through the openings 8 into the container 7 (see FIGS. 8 and 9). The excess bone cement paste 38 can be enclosed in the container 7 with the assistance of the lid 9.

Figure 10:
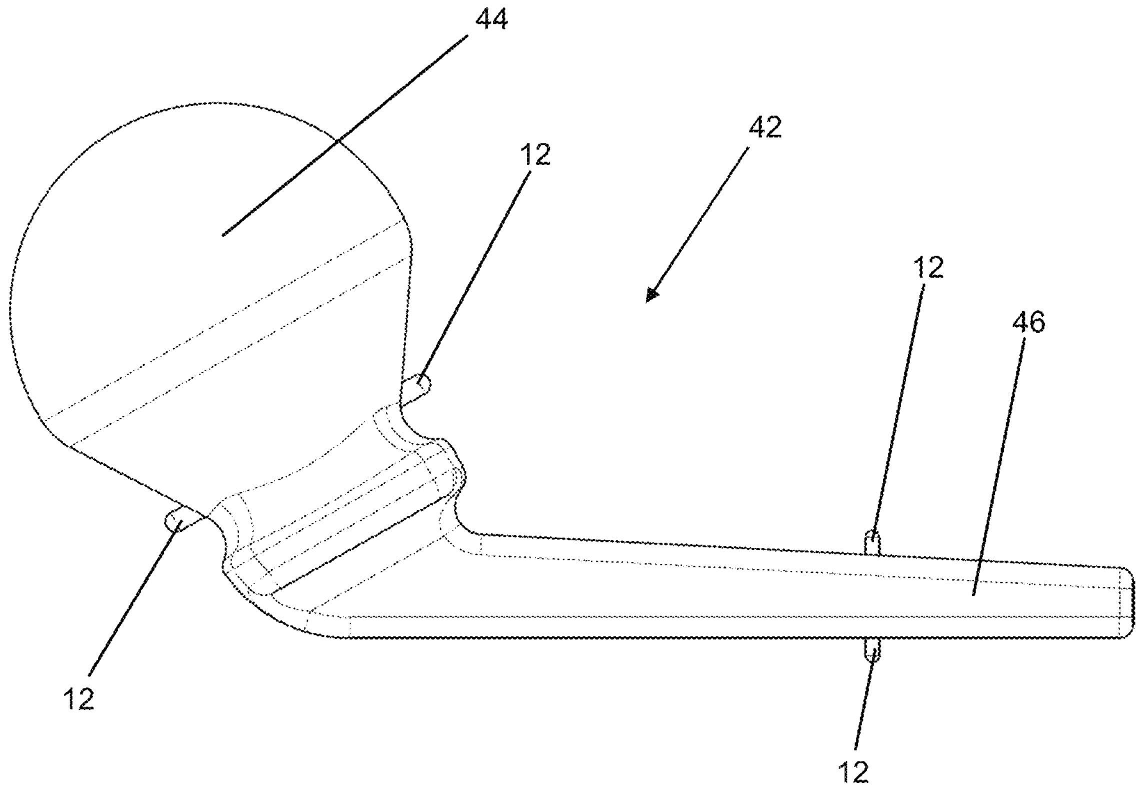
FIG. 10 shows a schematic perspective side view onto a spacer which has been produced using the device of the first exemplary embodiment according to FIGS. 1 to 9.
Figure 11:
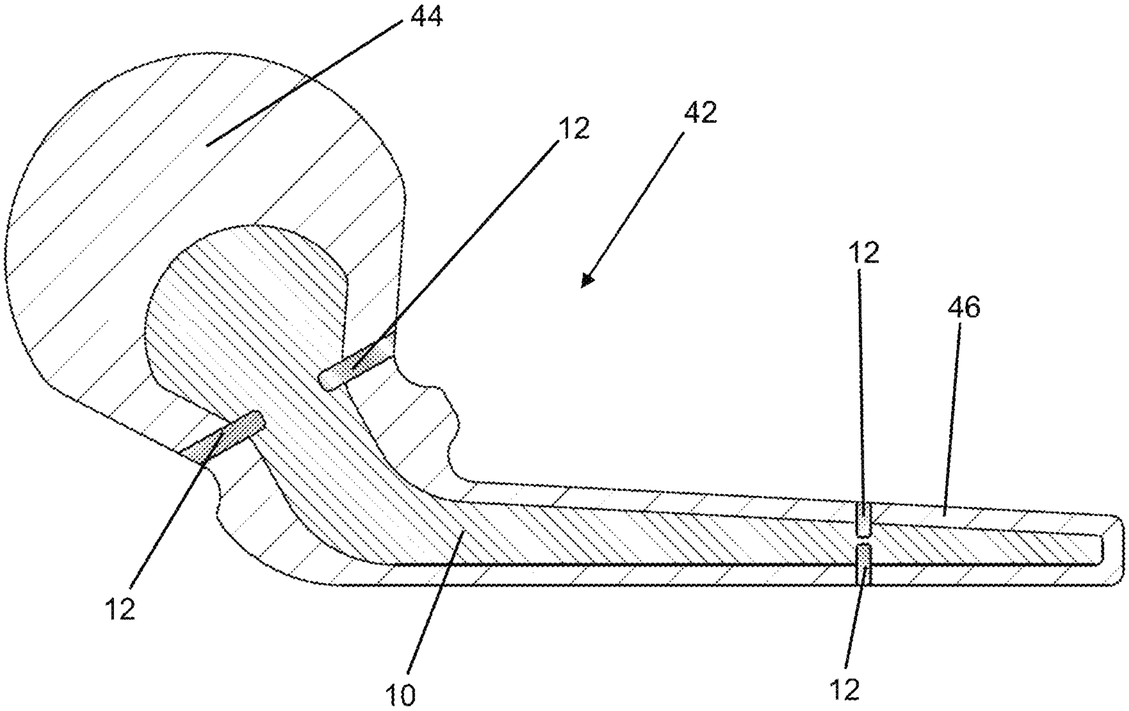
FIG. 11 shows a schematic cross-sectional view onto the spacer according to FIG. 10 with detached spacing pieces.

The bone cement paste 36 can then cure in the casting mold, wherein the surface thereof is molded by the surface of the cavity 2 of the casting mold lower part 1 and the shaping surface 6 of the casting mold upper part 5. The spacer 42, as shown for example in FIGS. 10 and 11, is obtained as a result. During curing of the bone cement paste 36, sprues 40, which connect the spacer 42 with the cured excess bone cement paste 38 in the container 7, may be formed in the openings 8. The spacer 42 is demolded by being detached from the casting mold lower part 1 and the casting mold upper part 5. In so doing, the sprues 40 may be sheared off or broken off. In order to ensure straightforward demolding, the sprues 40 must be of such a small diameter that they can be broken off or sheared off manually when the spacer 42 is separated from casting mold upper part 5. It has proven effective to this end for the sprues 40 to have a diameter of a maximum of 2.5 cm and preferably of a maximum of 2 cm. Accordingly, the openings 8 should have an internal diameter of a maximum of 2.5 cm and preferably a maximum of 2 cm. Smaller diameters may also be selected in order to further simplify separation of the sprues 40. The openings 8 should, however, not have a diameter of less than 0.2 mm so that the bone cement paste 36 can still be pressed out through the openings 8 without excessive resistance. Otherwise, depending on the viscosity of the bone cement paste 36, the resistance when pushing the casting mold upper part 5 into the casting mold lower part 1 may become too great for it still to be possible to be carried out manually or for damage to or destruction of the casting mold to be avoided. The optimum diameter of the openings 8 here depends on the viscosity of the bone cement paste 36 which is used. Highly suitable diameters for typical bone cements are between 1 mm and 20 mm. As a rule of thumb, the higher the viscosity of the bone cement paste 36, the larger the selected internal diameter of the openings 8 should be.

After demolding, the projecting spacing pieces 12, any flash which has formed at the junction between the casting mold lower part 1 and the casting mold upper part 5, and protruding residues of the sprues 40 may be removed, for example by being trimmed off with a knife or scalpel or by being ground off with a grinding head. The spacer 42, as shown in FIG. 11, is obtained as the final result.

FIGS. 12 to 22 are drawings showing various views of a second exemplary embodiment of a device according to the invention for producing a spacer for a shoulder joint, parts of the device and a spacer produced using the device. FIGS. 12 to 18 and 22 show the course of a second exemplary embodiment of a method according to the invention which is carried out using the device according to the second exemplary embodiment.

The second device according to the invention is suitable and provided for producing a spacer 92 (see FIGS. 17 and 18) fora shoulder joint. The device comprises a multipart casting mold. The casting mold has a casting mold lower part 51 and a casting mold upper part 55. A cavity 52 for receiving bone cement paste 36 (see FIGS. 12 to 15) and for forming part of the surface of the spacer 92 to be produced is arranged in the casting mold lower part 51. The cavity 52 can shape one half of the spacer 92. A casting mold wall 53, which extends the hollow space formed by the cavity 52 with an interior 54, may be arranged at the edge of the cavity 52. The casting mold wall 53 may to this end peripherally enclose the edge of the cavity 52. The walls of the casting mold wall 53 may be oriented parallel to one another, such that the casting mold wall 53 has a generally cylindrical geometry, wherein the base area of the general cylinder is defined by the area which delimits the edge of the cavity 52. The interior 54 for introduction of bone cement paste 36 is arranged within the walls of the casting mold wall 53, which interior is connected, and preferably also aligned, with the cavity 52.

The casting mold upper part 55 may preferably be inserted or pushed into the casting mold lower part 51. The casting mold upper part 55 has at the bottom thereof a shaping surface 56, with which a further part of the surface of the spacer 92 to be produced is shapeable and preferably the remaining part of the surface of the spacer 92 to be produced is shapeable. Together with the cavity 52, the shaping surface 56 may define the entire surface of the spacer 92 or at least 90% of the entire surface of the spacer 92. The shaping surface 56 may form an indentation in the casting mold upper part 55. It is also possible for part of the casting mold wall 53 to form part of the surface of the spacer 92 or for one or more inserts (not shown), which shape part of the surface of the spacer 92, additionally to be inserted into the cavity 52 and/or placed on the shaping surface 56.

A container 57 for receiving excess bone cement paste 38 (see FIG. 22) may be arranged on the side of the casting mold upper part 55 opposite from the shaping surface 56. Openings 58, which provide a through-connection for the excess bone cement paste 38 from the side of the shaping surface 56 to the container 57, may be present in the shaping surface 56. The openings 58 are preferably arranged at the points of the shaping surface 56 which, in the proper disposition of the device, are the highest shaping points of the casting mold. In this way, gases entrapped in the casting mold may escape through the openings 58 such that entrapped air is avoided in the spacer 92 to be produced.

The container 57 may have been or be impermeably closed to the outside for the bone cement paste 36 with a lid 59. An internal wall 61, which delimits the container 57, may start from and extend away from the back face of the shaping surface 56. The internal wall 61 may align externally with a perfect fit with the casting mold wall 53. In this way, the casting mold upper part 55 can be inserted with a perfect fit into the casting mold wall 53 of the casting mold lower part 51 and the bone cement paste 36 accordingly collected from the inside of the casting mold wall 53 and pressed into the cavity 52 and the shaping surface 56. It may also be sufficient to this end if the casting mold wall 53 tapers in the direction of the cavity 52, wherein the taper must to this end have an acute angle.

The container 57 may be gas-permeably connected with the surroundings. Provision may be made to this end for the lid 59 not to close pressure-tightly and/or for small vent openings (not visible in the figures) to be arranged in the lid and/or the internal wall 61.

A metal core 60 may be provided as reinforcement for the spacer 92. The metal core 60 may to this end be held spaced from the internal side of the cavity 52 and from the casting mold wall 53 with the assistance of pin-shaped spacing pieces 62 of cured PMMA, such that the bone cement paste 36 can flow completely around the metal core 60 between the metal core 60 on the one hand and the internal side of the cavity 52 and the shaping surface 56 on the other. In order to position the spacing pieces 62, bores (not visible) may be provided in the metal core 60 for receiving one end of the pin-shaped spacing pieces 62. Matching indentations for receiving the opposite end of the pin-shaped spacing pieces 62 may likewise be arranged in the internal side of the cavity 52.

A stand 66, into which the casting mold lower part 51 may be placed or inserted, may be provided in order to position the casting mold correctly with the casting mold lower part 51 underneath and the casting mold wall 53 perpendicularly on top. The stand 66 may be provided for placement on a flat surface such as a table.

The casting mold lower part 51, the casting mold upper part 55, the lid 59 and the stand 66 may be inexpensively produced from a plastics film or a plurality of joined together plastics films, in particular by injection molding or by thermoforming. In the assembled state, the parts of the device produced from the plastics films stabilize one another mechanically. The plastics film(s) preferably consist of a polyolefin, a polyethylene (PET) or a glycol-modified PET (PETG). When a plurality of films are used, they may be laminated together with an adhesive or by elevated temperature.

Internally located grooves 68 and externally located sprues 69, which extend from a limit stop 70 on the side of the casting mold wall 53 opposite from the cavity 52 down to the edge of the cavity 52, may be arranged in the casting mold wall 53. The sprues 69 may contain the volume for forming the grooves 68. The ends of the pin-shaped spacing pieces 62, which project out of the metal core 60, may be guided to the cavity 52 along these grooves 68.

Grooves 71 matching the sprues 69 may be provided internally in the stand 66. As a result, the casting mold lower part 51 can be pushed in guided manner into the stand 66 and the casting mold lower part 51 does not so readily become detached from the stand 66 and does not move so easily relative to the stand 66.

In order to fix the spacing pieces 62 and thus the metal core 60 in place, matching recesses 73 may be arranged at the edge of the shaping surface 56 of the casting mold upper part 55. The recesses 73 may be arranged at the edge of the shaping surface 56 in such a manner that they are moved along the grooves 68 of the casting mold wall 53 when the casting mold upper part 55 is pushed into the casting mold wall 53 of the casting mold lower part 51. The ends of the spacing pieces 62 which project out from the metal core 60 are accordingly clamped in place in the casting mold between the casting mold upper part 55 and the casting mold lower part 51.

The limit stop 70 may be arranged as a peripheral strip-shaped edge projecting out perpendicularly from the casting mold wall 53 on the side of the casting mold wall 53 remote from the cavity 52. The limit stop 70 can limit how far the casting mold upper part 55 can be pushed into the casting mold lower part 51. The casting mold upper part 55 may to this end have a mating stop 72 in the form of a peripheral edge which projects out perpendicularly from the internal wall 61 and is arranged on the side of the internal wall 61 opposite from the shaping surface 56. When the casting mold upper part 55 has been completely pushed into the casting mold lower part 51, the mating stop 72 rests against the limit stop 70. In the same way, a lid edge 74 which can be placed on the side of the mating stop 72 opposite from the limit stop 70 may be arranged on the lid 59. Because the limit stop 70, the mating stop 72 and the lid edge 74 project out from the adjoining parts at an angle, the shape of the casting mold lower part 51, the casting mold upper part 55 and the lid 59 is mechanically stabilized in the assembled state. This is in particular helpful if these parts have been fabricated from a plastics film or a plurality of plastics films by thermoforming.

Figure 14:
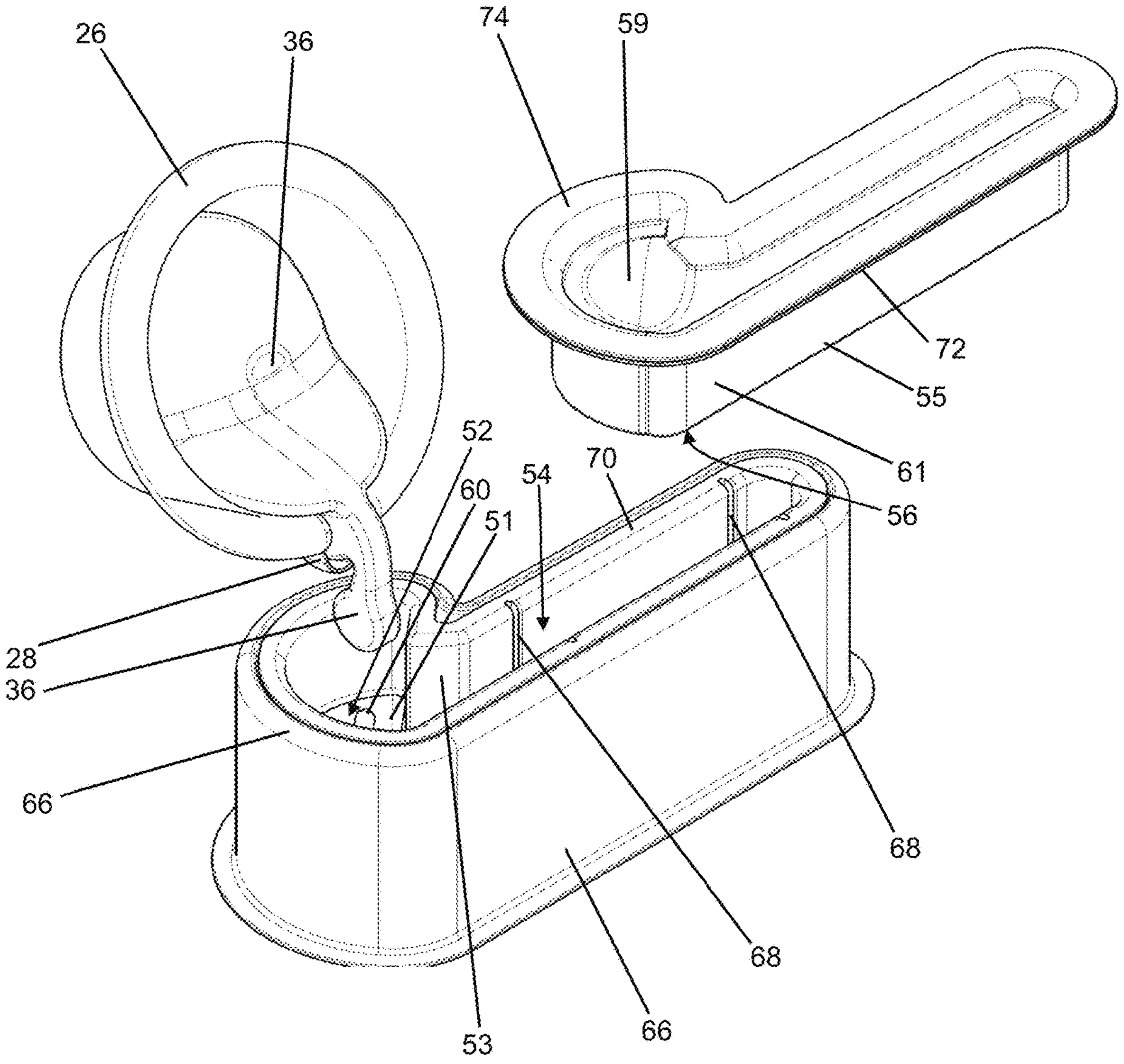
FIG. 14 shows a schematic perspective external view of the casting mold of the second exemplary embodiment during the introduction of bone cement paste.
Figure 15:
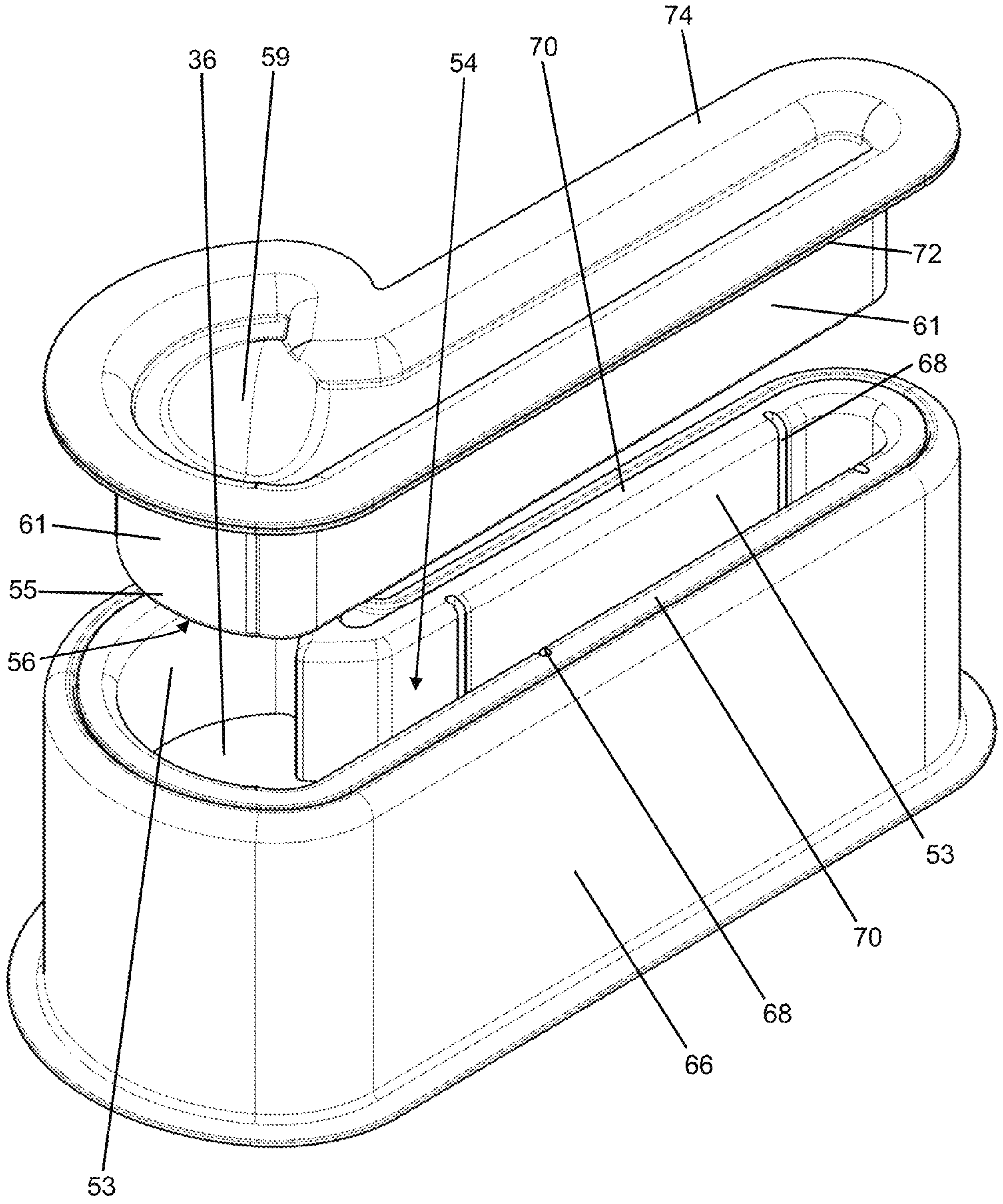
FIG. 15 shows a schematic perspective external view of the second exemplary embodiment prior to insertion of the casting mold upper part into the casting mold lower part.

The device may furthermore include a mixing cup 26 with a spout 28 for pouring bone cement paste 36 from the mixing cup 26 (see FIG. 14). The device may also include the starting components (not shown) of the bone cement paste 36 in separate containers. The bone cement paste 36 may then be mixed in the mixing cup 26 before it is introduced into the casting mold or into the casting mold lower part 51. The bone cement paste 36 may, however, also be produced in another way before it is introduced into the casting mold. The device thus does not necessarily require the mixing cup 26 and also not the bone cement paste 36 or the starting components thereof. The device may in principle be applied and used with any other known system for producing a bone cement paste, such as for example with a suitable cartridge system for storing and mixing bone cement paste.

The course of a first exemplary embodiment of a method according to the invention is described below with reference to FIGS. 12 to 22.

Figure 12:
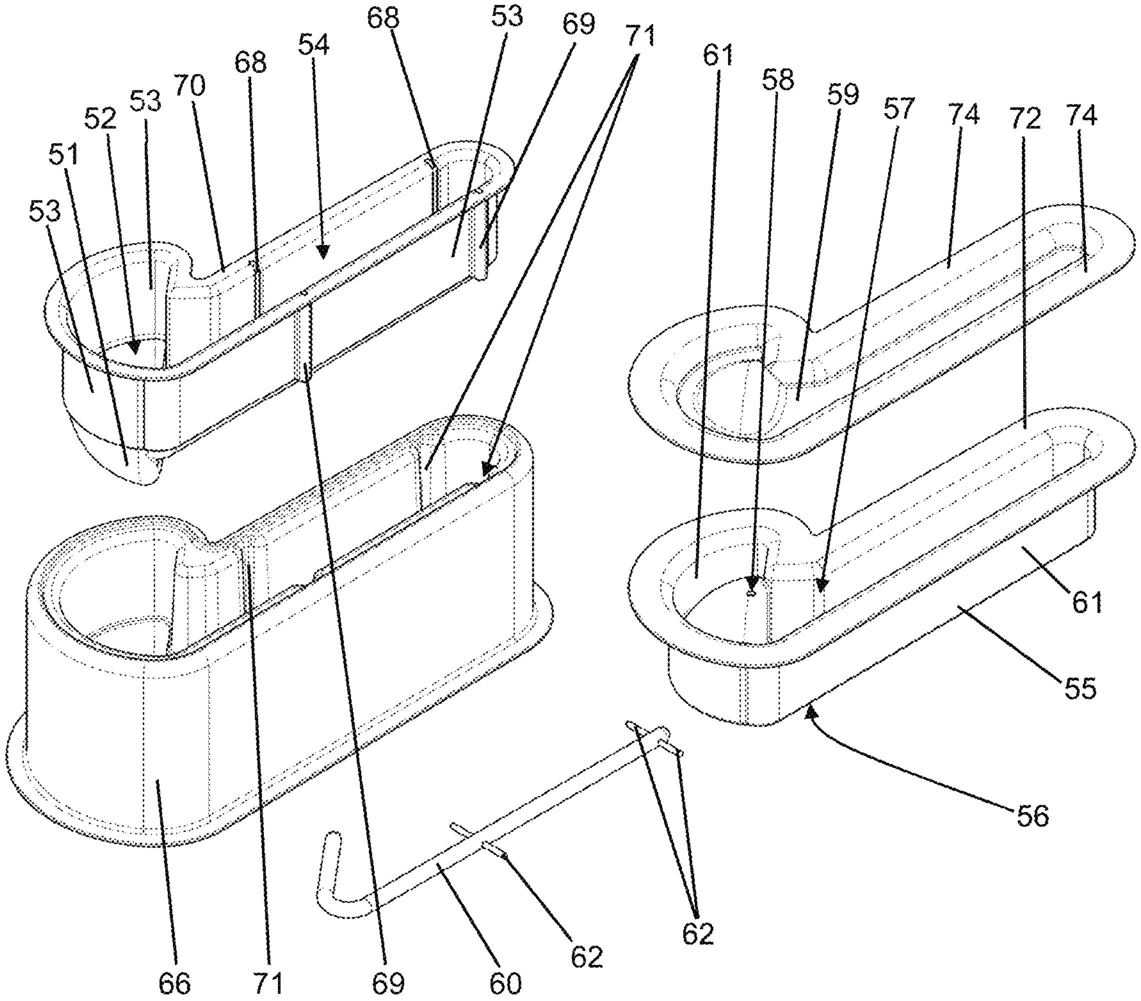
FIG. 12 shows a schematic perspective view onto the individual parts of a second exemplary embodiment of the present invention as a device for producing a spacer for a shoulder joint.
Figure 13:
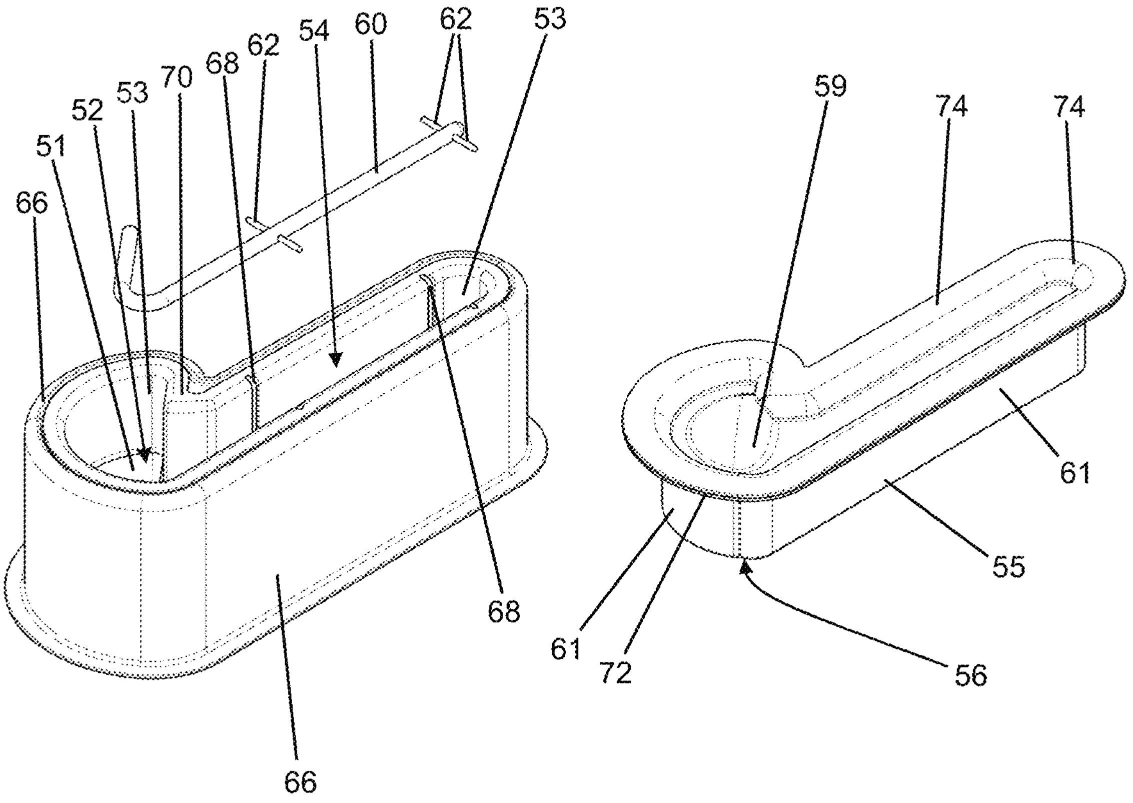
FIG. 13 shows a schematic perspective external view of the second exemplary embodiment according to FIG. 12 prior to arrangement of the metal core in the casting mold lower part.

The device may firstly be removed from a package (not shown) in a sterile state and may then be present as shown in FIG. 12 or in FIG. 13. If the casting mold lower part 51 has not already been inserted into the stand 66, the casting mold lower part 51 may be pushed into the stand 66 via the grooves 71. If not already present therein, the metal core 60 may be inserted into the cavity 52 (see FIG. 13). In so doing, the projecting ends of the spacing pieces 62 slide in the grooves 68 of the casting mold wall 53.

When the metal core 60 is inserted into the cavity 52 or into the interior 54, the bone cement paste 36 can be introduced in excess into the interior 54 and the cavity 52 (see FIG. 14). The casting mold upper part 55 may then be inserted and pushed into the casting mold lower part 51 or into the casting mold wall 53. The container 57 may to this end be closed with the lid 59 (see FIG. 15).

Figure 16:
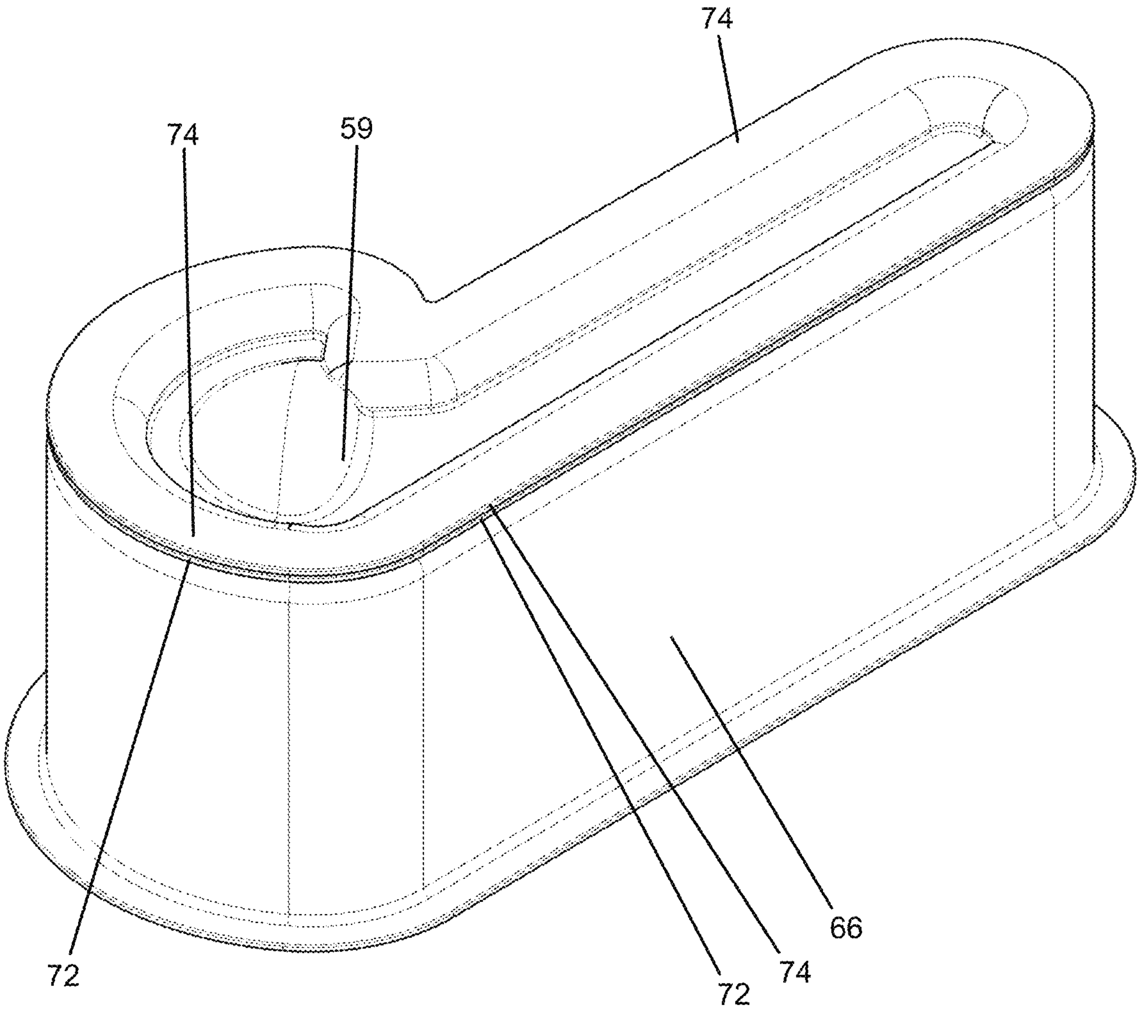
FIG. 16 shows a schematic perspective view onto the closed casting mold of the second exemplary embodiment.
Figure 20:
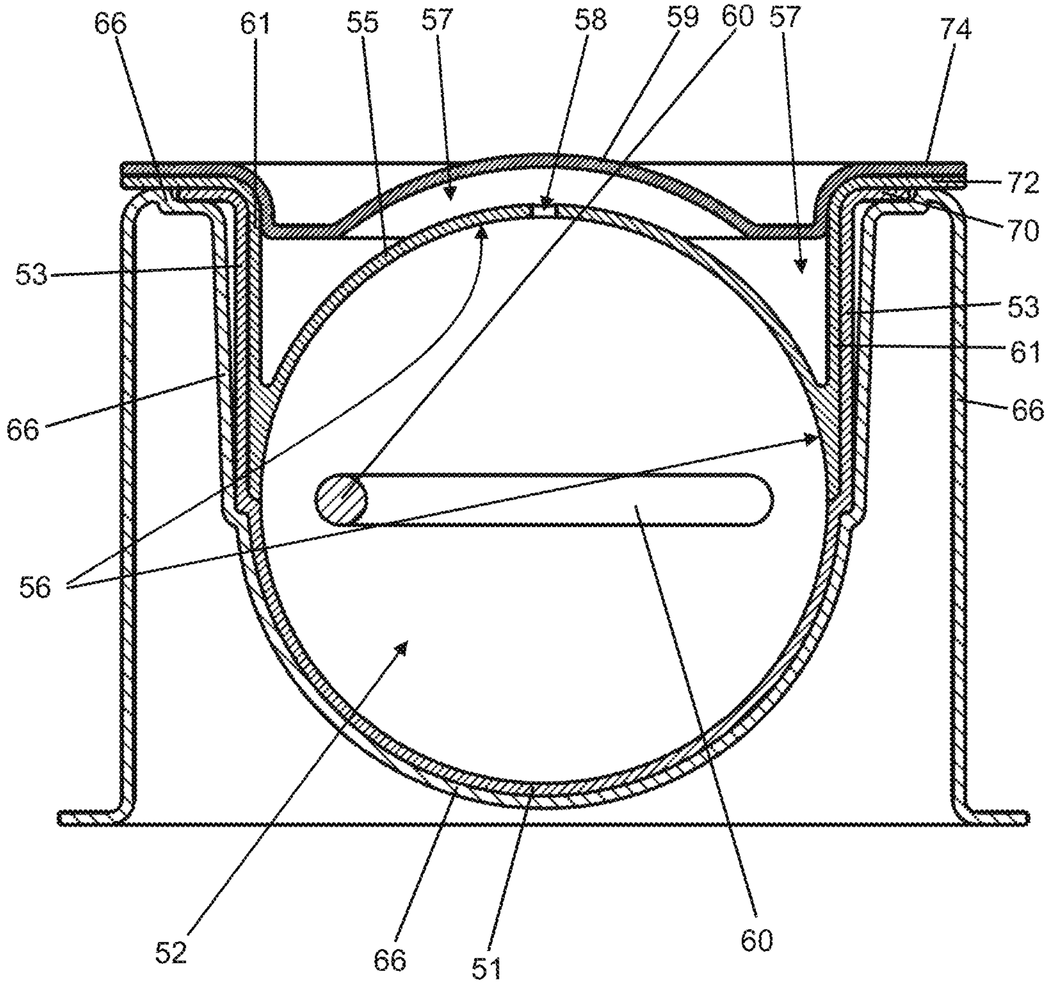
FIG. 20 shows a schematic cross-sectional view onto section B according to FIG. 19 of the second exemplary embodiment in the closed state.
Figure 21:
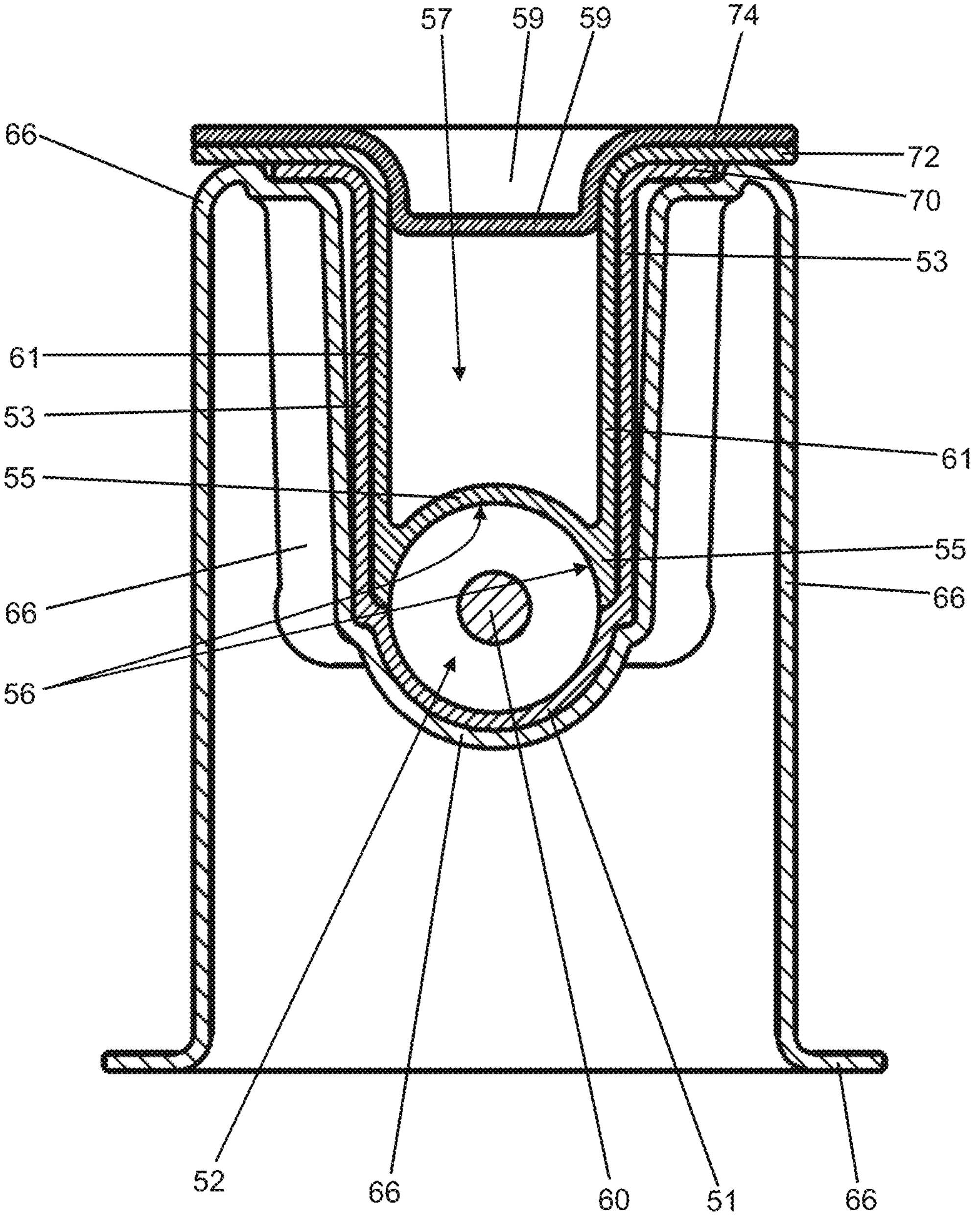
FIG. 21 shows a schematic cross-sectional view onto section A according to FIG. 19 of the second exemplary embodiment in the closed state.
Figure 22:
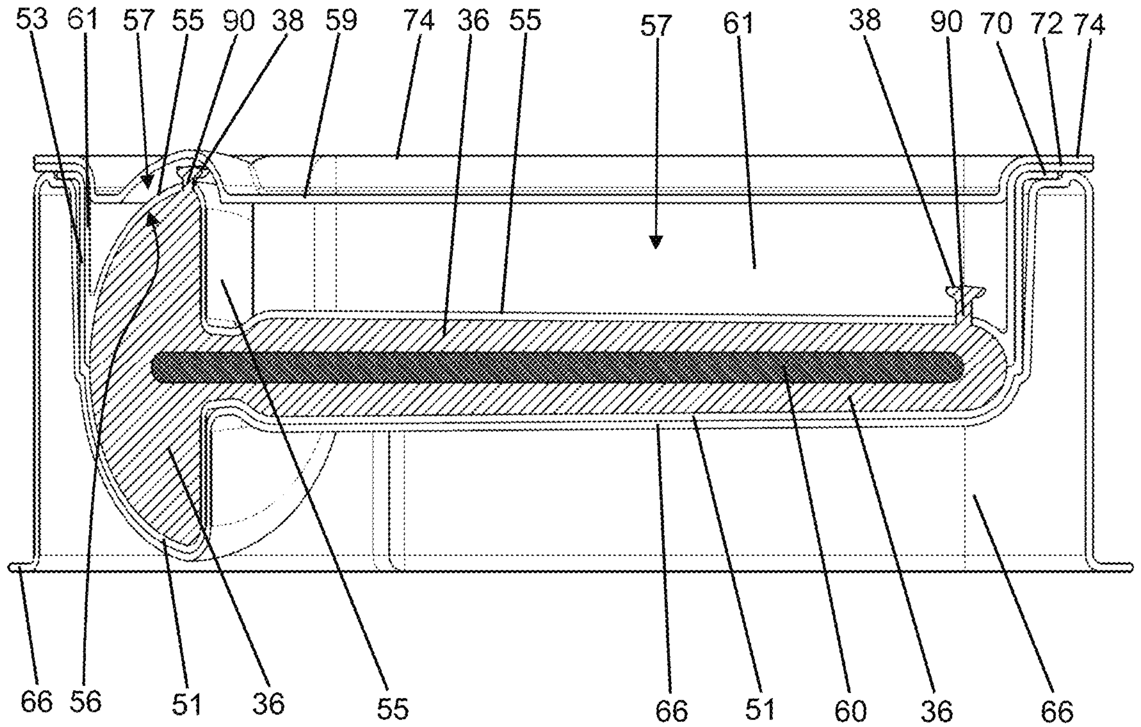
FIG. 22 shows a schematic perspective cross-sectional view onto the casting mold filled with bone cement paste of the second exemplary embodiment in the closed state.

The casting mold upper part 55 may be pushed into the interior 54 of the casting mold lower part 51 until the mating stop 72 rests against the limit stop 70 (see to this end FIGS. 16, 20 and 21, which either do not show the bone cement paste enclosed in the casting mold (FIGS. 20 and 21) or in which it is not visible (FIG. 16)). When the casting mold upper part 55 is pushed in, the bone cement paste 36 which is present may be pressed into the cavity 52 and the volume within the casting mold continuously decreases. Excess bone cement paste 38 is pressed out through the openings 58 into the container 57 (see FIG. 22). The excess bone cement paste 38 can be enclosed in the container 57 with the assistance of the lid 59.

Figure 17:
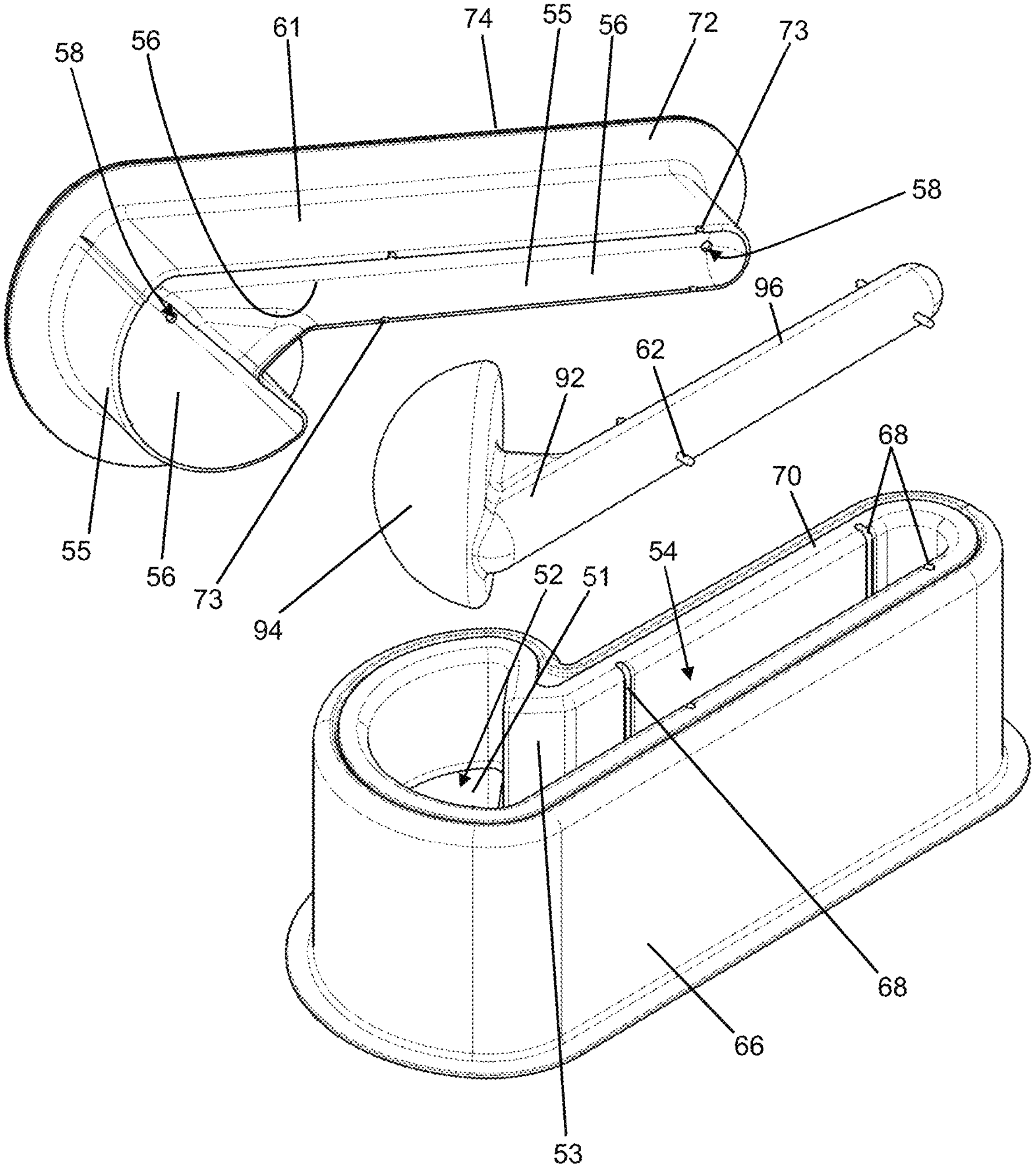
FIG. 17 shows a schematic perspective view of the first exemplary embodiment during removal of the cured spacer.
Figure 18:
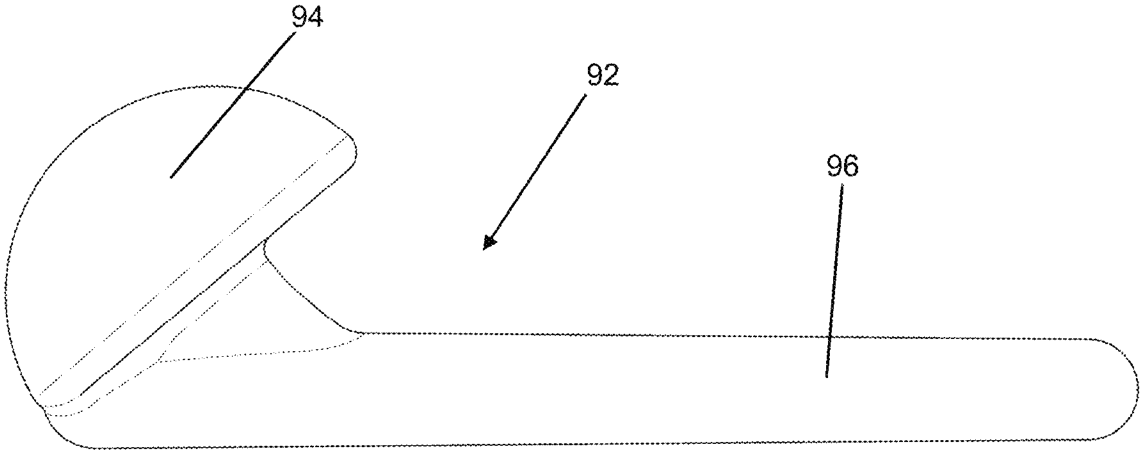
FIG. 18 shows a schematic perspective side view onto the spacer which has been produced using the device of the second exemplary embodiment according to FIGS. 12 to 17.
Figure 19:
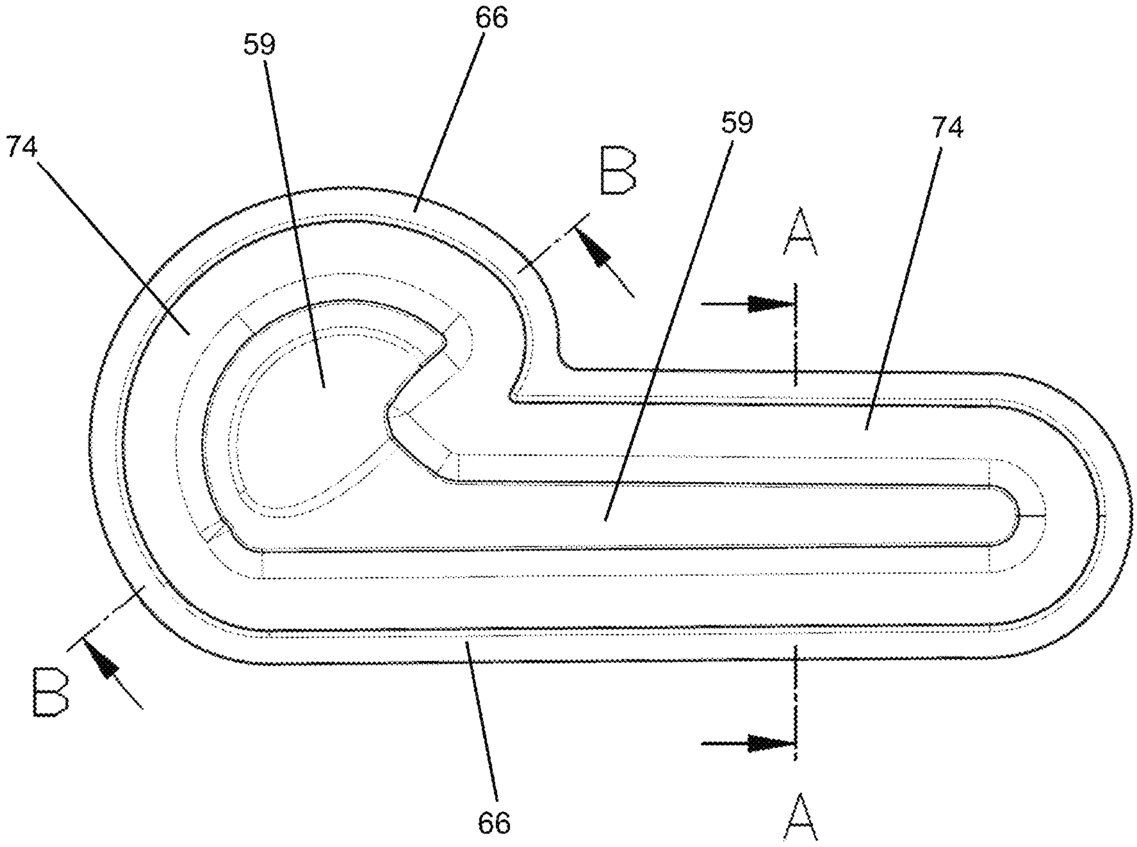
FIG. 19 shows a schematic plan view onto the closed casting mold of the second exemplary embodiment with section planes A and B indicated.

The bone cement paste 36 can then cure in the casting mold, wherein the surface thereof is molded by the surface of the cavity 52 of the casting mold lower part 51 and the shaping surface 56 of the casting mold upper part 55. The spacer 92, as shown for example in FIGS. 17 and 18, is obtained as a result. During curing of the bone cement paste 36, sprues 90, which connect the spacer 92 with the cured excess bone cement paste 38 in the container 57, may be formed in the openings 58. The spacer 92 is demolded by being detached from the casting mold lower part 51 and the casting mold upper part 55. In so doing, the sprues 90 may be sheared off or broken off. In order to ensure straightforward demolding, the sprues 90 must be of such a small diameter that they can be broken off or sheared off manually when the spacer 92 is separated from casting mold upper part 55. It has proven effective to this end for the sprues 90 to have a diameter of a maximum of 2.5 cm and preferably of a maximum of 2 cm. Accordingly, the openings 58 should have an internal diameter of a maximum of 2.5 cm and preferably a maximum of 2 cm. Smaller diameters may also be selected in order to further simplify separation of the sprues 90. The openings 58 should, however, not have a diameter of less than 0.2 mm so that the bone cement paste 36 can still be pressed out through the openings 58 without excessive resistance. Otherwise, depending on the viscosity of the bone cement paste 36, the resistance when pushing the casting mold upper part 55 into the casting mold lower part 51 may become too great for it still to be possible to be carried out manually or for damage to or destruction of the casting mold to be avoided. The optimum diameter of the openings 58 here depends on the viscosity of the bone cement paste 36 which is used. Highly suitable diameters for typical bone cements are between 1 mm and 20 mm. As a rule of thumb, the higher the viscosity of the bone cement paste 36, the larger the selected internal diameter of the openings 58 should be.

After demolding, the projecting spacing pieces 62, any flash which has formed at the junction between the casting mold lower part 51 and the casting mold upper part 55, and protruding residues of the sprues 90 may be removed, for example by being trimmed off with a knife or scalpel or by being ground off with a grinding head. The spacer 92, as shown in FIG. 18, is obtained as the final result.

FIGS. 23 to 35 are drawings showing various views of a third exemplary embodiment of a device according to the invention for producing a spacer for a knee joint, parts of the spacer and parts of the device. FIGS. 23 to 31 show the course of a third exemplary embodiment of a method according to the invention which is carried out using the device according to the third exemplary embodiment.

The third device according to the invention is suitable and provided for producing a two-part articulating spacer with a spacer 142 for the femur and a spacer 192 for the tibia (see FIGS. 31 and 34) for replacing a knee joint. The device has two multipart casting molds, a femoral component casting mold for producing the spacer 142 for the femur (on the left in FIGS. 23 to 28 and 30 to 32 and 35 and at the top in FIGS. 29 and 33) and a tibial component casting mold for producing the spacer 192 for the tibia (on the right in FIGS. 23 to 28 and 30 to 32 and 35 and at the bottom in FIGS. 29 and 33). The third exemplary embodiment may for the purposes of the present invention also be understood as two different devices according to the invention, namely as a fourth device for producing a spacer 142 for the femur and a fifth device for producing a spacer 192 for the tibia.

The femoral component casting mold has a casting mold lower part 101 and a casting mold upper part 105. A cavity 102 for receiving bone cement paste 36 (see FIGS. 23 to 25, 29 and 33) and for forming part of the surface of the spacer 142 to be produced is arranged in the casting mold lower part 101. The cavity 102 can shape one half of the spacer 142. A casting mold wall 103, which extends the hollow space formed by the cavity 102 with an interior 104, may be arranged at the edge of the cavity 102. The casting mold wall 103 may to this end peripherally enclose the edge of the cavity 102. The walls of the casting mold wall 103 may be oriented parallel to one another, such that the casting mold wall 103 has a generally cylindrical geometry, wherein the base area of the general cylinder is defined by the area which delimits the edge of the cavity 102. The interior 104 for introduction of bone cement paste 36 is arranged within the walls of the casting mold wall 103, which interior is connected, and preferably also aligned, with the cavity 102.

The casting mold upper part 105 may preferably be inserted or pushed into the casting mold lower part 101. The casting mold upper part 105 has at the bottom thereof a shaping surface 106, with which a further part of the surface of the spacer 142 to be produced is shapeable and preferably the remaining part of the surface of the spacer 142 to be produced is shapeable. Together with the cavity 102, the shaping surface 106 may define the entire surface of the spacer 142 or at least 90% of the entire surface of the spacer 142. The shaping surface 106 may form an indentation in the casting mold upper part 105. It is also possible for part of the casting mold wall 103 to form part of the surface of the spacer 142 or for one or more inserts (not shown), which shape part of the surface of the spacer 142, additionally to be inserted into the cavity 102 and/or placed on the shaping surface 106.

A container 107 for receiving excess bone cement paste 38 (see FIG. 29) may be arranged on the side of the casting mold upper part 105 opposite from the shaping surface 106. Openings 108, in the form of channels in an internal wall 111 of the casting mold upper part 105, which provide a through-connection for the excess bone cement paste 38 from the side of the shaping surface 106 to the container 107, may be present in the shaping surface 106. The openings 108 are preferably arranged at the points of the shaping surface 106 which, in the proper disposition of the device, are the highest shaping points of the femoral component casting mold. In this way, gases entrapped in the femoral component casting mold may escape through the openings 108 such that entrapped air is avoided in the spacer 142 to be produced.

The container 107 may have been or be impermeably closed to the outside for the bone cement paste 36 with a lid 109. The internal wall 111, which delimits the container 107, may start from and extend away from the back face of the shaping surface 106. The internal wall 111 may align externally with a perfect fit with the casting mold wall 103. In this way, the casting mold upper part 105 can be inserted with a perfect fit into the casting mold wall 103 of the casting mold lower part 101 and the bone cement paste 36 accordingly collected from the inside of the casting mold wall 103 and pressed into the cavity 102 and the shaping surface 106. It may also be sufficient to this end if the casting mold wall 103 tapers in the direction of the cavity 102, wherein the taper must to this end have an acute angle.

The container 107 may be gas-permeably connected with the surroundings. Provision may be made to this end for the lid 109 not to close pressure-tightly and/or for small vent openings (not visible in the figures) to be arranged in the lid and/or the internal wall 111.

Figure 32:
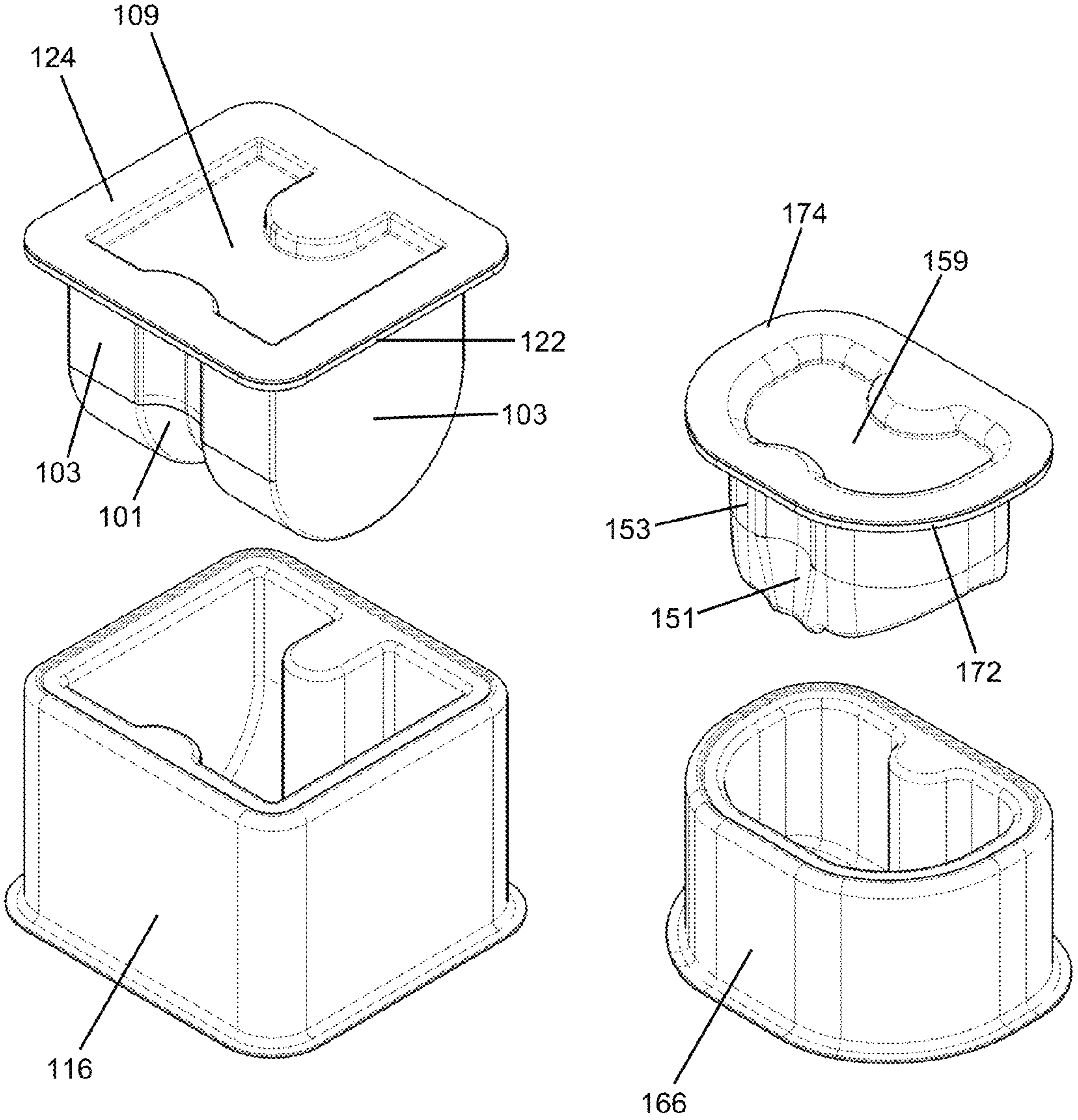
FIG. 32 shows a schematic perspective view of the third exemplary embodiment with closed casting molds and stands for the casting molds.
Figure 33:
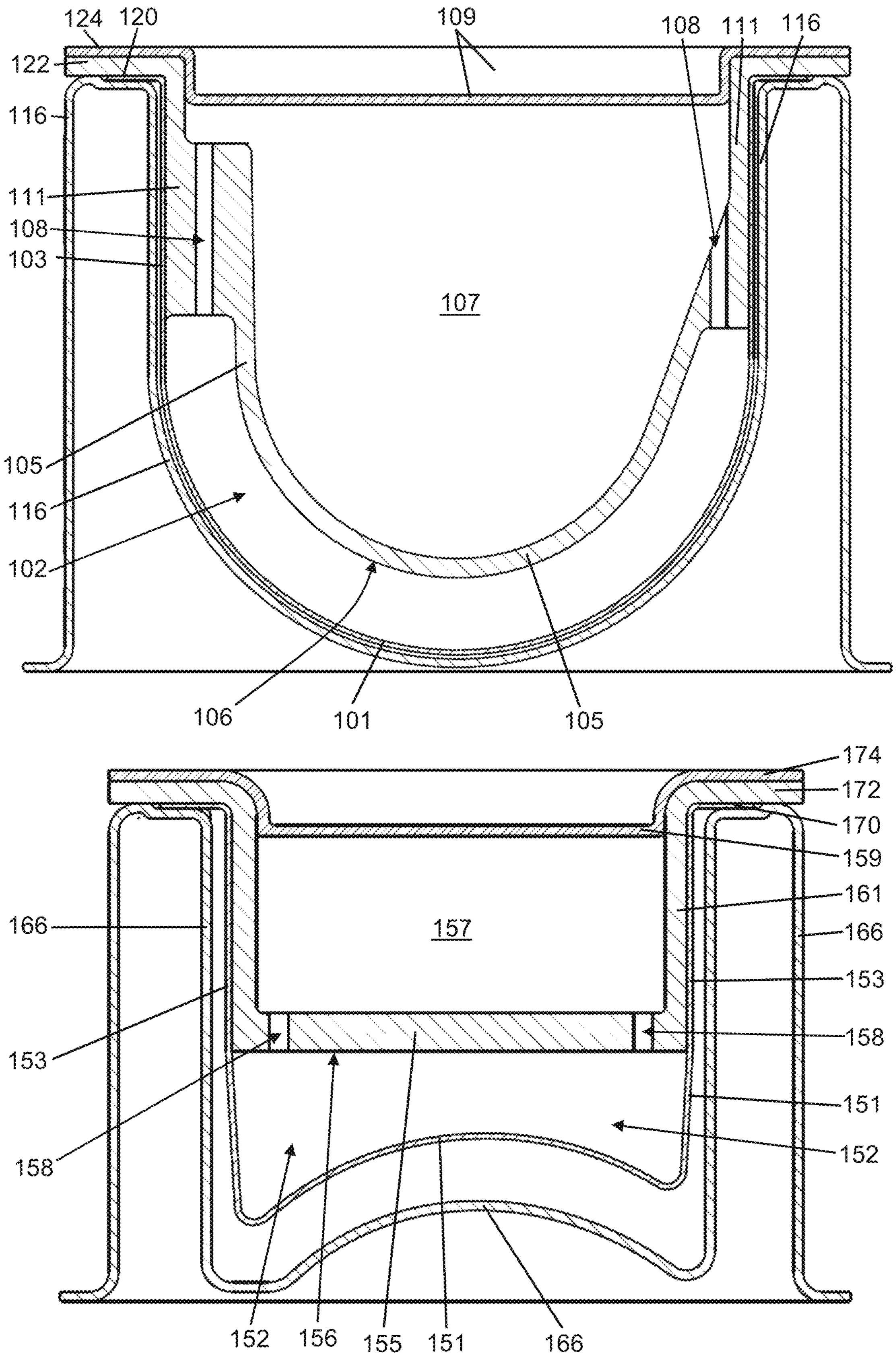
FIG. 33 shows a schematic cross-sectional view of the casting molds of the third exemplary embodiment in the closed state.

According to a preferred variant of the third exemplary embodiment, a stand 116, into which the casting mold lower part 101 may be placed or inserted, may be provided for correctly positioning the femoral component casting mold with the casting mold lower part 101 underneath and the casting mold wall 103 perpendicularly on top (see FIGS. 32 and 33). The stand 116 may be provided for placement on a flat surface such as a table.

The casting mold lower part 101, the casting mold upper part 105, the lid 109 and the stand 116 may be inexpensively produced from a plastics film or a plurality of joined together plastics films, in particular by injection molding or by thermoforming. In the assembled state, the parts of the device produced from the plastics films stabilize one another mechanically. The plastics film(s) preferably consist of a polyolefin, a polyethylene (PET) or a glycol-modified PET (PETG). When a plurality of films are used, they may be laminated together with an adhesive or by elevated temperature.

A limit stop 120 may be arranged as a peripheral strip-shaped edge projecting out perpendicularly from the casting mold wall 103 on the side of the casting mold wall 103 remote from the cavity 102. The limit stop 120 can limit how far the casting mold upper part 105 can be pushed into the casting mold lower part 101. The casting mold upper part 105 may to this end have a mating stop 122 in the form of a peripheral edge which projects out perpendicularly from the internal wall 111 and is arranged on the side of the internal wall 111 opposite from the shaping surface 106. When the casting mold upper part 105 has been completely pushed into the casting mold lower part 101, the mating stop 122 rests against the limit stop 120. In the same way, a lid edge 124 which can be placed on the side of the mating stop 122 opposite from the limit stop 120 may be arranged on the lid 109. Because the limit stop 120, the mating stop 122 and the lid edge 124 project out from the adjoining parts at an angle, the shape of the casting mold lower part 101, the casting mold upper part 105 and the lid 109 is mechanically stabilized in the assembled state. This is in particular helpful if these parts have been fabricated from a plastics film or a plurality of plastics films by thermoforming.

The tibial component casting mold is of similar construction to the femoral component casting mold and has a casting mold lower part 151 and a casting mold upper part 155. A cavity 152 for receiving bone cement paste 36 (see FIGS. 23 to 25, 29 and 33) and for forming part of the surface of the spacer 192 to be produced is arranged in the casting mold lower part 151. The cavity 152 can shape one half of the spacer 192. A casting mold wall 153, which extends the hollow space formed by the cavity 152 with an interior 154, may be arranged at the edge of the cavity 152. The casting mold wall 153 may to this end peripherally enclose the edge of the cavity 152. The walls of the casting mold wall 153 may be oriented parallel to one another, such that the casting mold wall 153 has a generally cylindrical geometry, wherein the base area of the general cylinder is defined by the area which delimits the edge of the cavity 152. The interior 154 for introduction of bone cement paste 36 is arranged within the walls of the casting mold wall 153, which interior is connected, and preferably also aligned, with the cavity 152.

The casting mold upper part 155 may preferably be inserted or pushed into the casting mold lower part 151. The casting mold upper part 155 has at the bottom thereof a shaping surface 156, with which a further part of the surface of the spacer 192 to be produced is shapeable and preferably the remaining part of the surface of the spacer 192 to be produced is shapeable. Together with the cavity 152, the shaping surface 156 may define the entire surface of the spacer 192 or at least 90% of the entire surface of the spacer 192. The shaping surface 156 may form an indentation in the casting mold upper part 155. It is also possible for part of the casting mold wall 153 to form part of the surface of the spacer 192 or for one or more inserts (not shown), which shape part of the surface of the spacer 192, additionally to be inserted into the cavity 152 and/or placed on the shaping surface 156.

A container 157 for receiving excess bone cement paste 38 (see FIG. 29) may be arranged on the side of the casting mold upper part 155 opposite from the shaping surface 156. Openings 158, which provide a through-connection for the excess bone cement paste 38 from the side of the shaping surface 156 to the container 157, may be present in the shaping surface 156. The openings 158 are preferably arranged at the points of the shaping surface 156 which, in the proper disposition of the device, are the highest shaping points of the tibial component casting mold. In this way, gases entrapped in the tibial component casting mold may escape through the openings 158 such that entrapped air is avoided in the spacer 192 to be produced.

The container 157 may have been or be impermeably closed to the outside for the bone cement paste 36 with a lid 159. An internal wall 161, which delimits the container 157, may start from and extend away from the back face of the shaping surface 156. The internal wall 161 may align externally with a perfect fit with the casting mold wall 153. In this way, the casting mold upper part 155 can be inserted with a perfect fit into the casting mold wall 153 of the casting mold lower part 151 and the bone cement paste 36 accordingly collected from the inside of the casting mold wall 153 and pressed into the cavity 152 and the shaping surface 156. It may also be sufficient to this end if the casting mold wall 153 tapers in the direction of the cavity 152, wherein the taper must to this end have an acute angle.

The container 157 may be gas-permeably connected with the surroundings. Provision may be made to this end for the lid 159 not to close pressure-tightly and/or for small vent openings (not visible in the figures) to be arranged in the lid and/or the internal wall 161.

According to a preferred variant of the third exemplary embodiment, a stand 166, into which the casting mold lower part 151 may be placed or inserted, may be provided for correctly positioning the tibial component casting mold with the casting mold lower part 151 underneath and the casting mold wall 153 perpendicularly on top (see FIGS. 32 and 33). The stand 166 may be provided for placement on a flat surface such as a table.

The casting mold lower part 151, the casting mold upper part 155, the lid 159 and the stand 166 may be inexpensively produced from a plastics film or a plurality of joined together plastics films, in particular by injection molding or by thermoforming. In the assembled state, the parts of the device produced from the plastics films stabilize one another mechanically. The plastics film(s) preferably consist of a polyolefin, a polyethylene (PET) or a glycol-modified PET (PETG). When a plurality of films are used, they may be laminated together with an adhesive or by elevated temperature.

A limit stop 170 may be arranged as a peripheral strip-shaped edge projecting out perpendicularly from the casting mold wall 153 on the side of the casting mold wall 153 remote from the cavity 152. The limit stop 170 can limit how far the casting mold upper part 155 can be pushed into the casting mold lower part 151. The casting mold upper part 155 may to this end have a mating stop 172 in the form of a peripheral edge which projects out perpendicularly from the internal wall 161 and is arranged on the side of the internal wall 161 opposite from the shaping surface 156. When the casting mold upper part 155 has been completely pushed into the casting mold lower part 151, the mating stop 172 rests against the limit stop 170. In the same way, a lid edge 174 which can be placed on the side of the mating stop 172 opposite from the limit stop 170 may be arranged on the lid 159. Because the limit stop 170, the mating stop 172 and the lid edge 174 project out from the adjoining parts at an angle, the shape of the casting mold lower part 151, the casting mold upper part 155 and the lid 159 is mechanically stabilized in the assembled state. This is in particular helpful if these parts have been fabricated from a plastics film or a plurality of plastics films by thermoforming.

The device may furthermore include a mixing cup 26 with a spout 28 for pouring bone cement paste 36 from the mixing cup 26 (see FIG. 23) and a film pouch 30 containing cement powder, an ampoule 32 containing monomer liquid and a spatula 34 for mixing the cement powder with monomer liquid in the mixing cup 26. The bone cement paste 36 may then be mixed in the mixing cup 26 before it is introduced into the casting mold or into the casting mold lower part 1. The bone cement paste 36 may, however, also be produced in another way before it is introduced into the casting mold. The device thus does not necessarily require the mixing cup 26 and also not the bone cement paste 36 or the starting components thereof. The device may in principle be applied and used with any other known system for producing a bone cement paste, such as for example with a suitable cartridge system for storing and mixing bone cement paste.

The course of a third exemplary embodiment of a method according to the invention is described below with reference to FIGS. 23 to 35.

Figure 23:
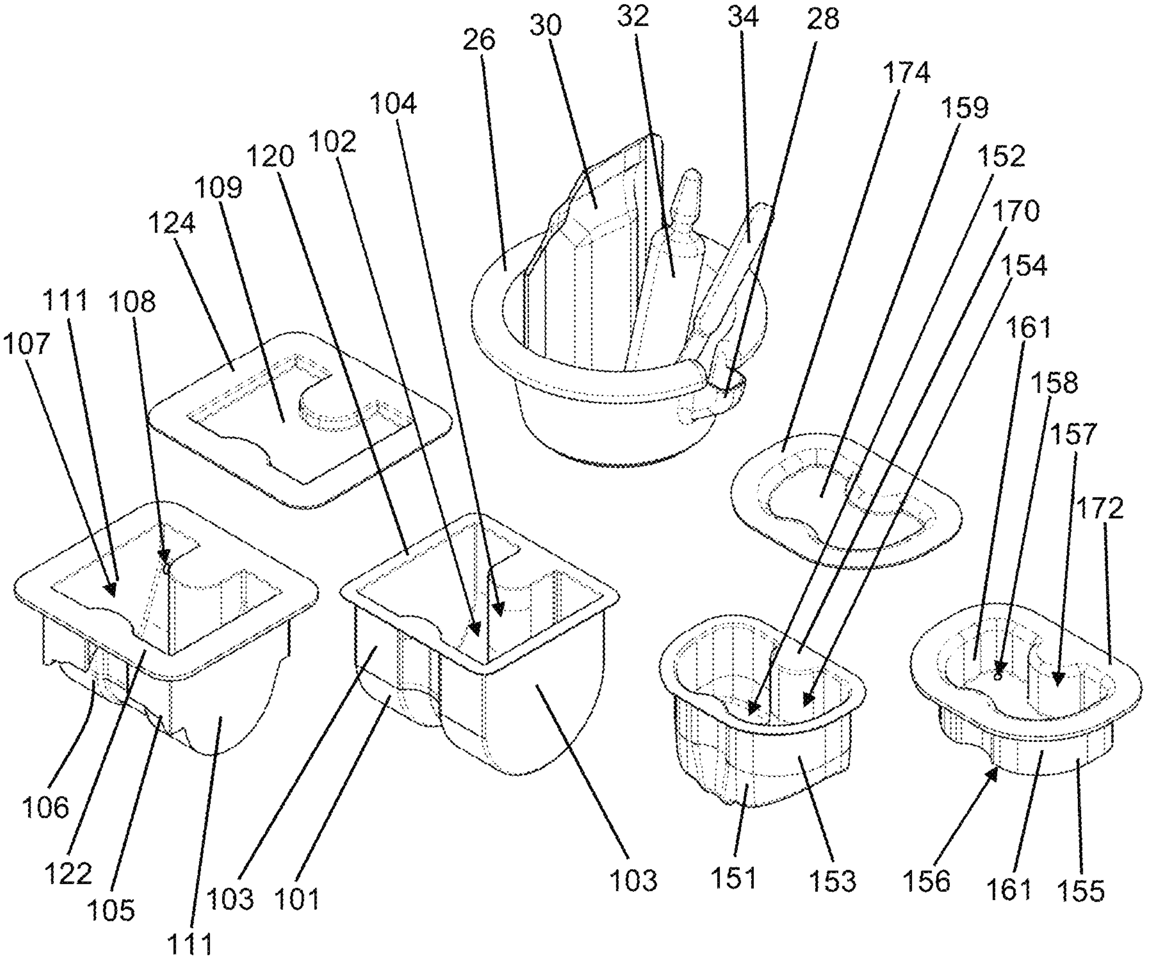
FIG. 23 shows a schematic perspective view onto the individual parts of a third exemplary embodiment of the present invention as a device for producing two components of an articulating spacer for a knee joint.
Figure 24:
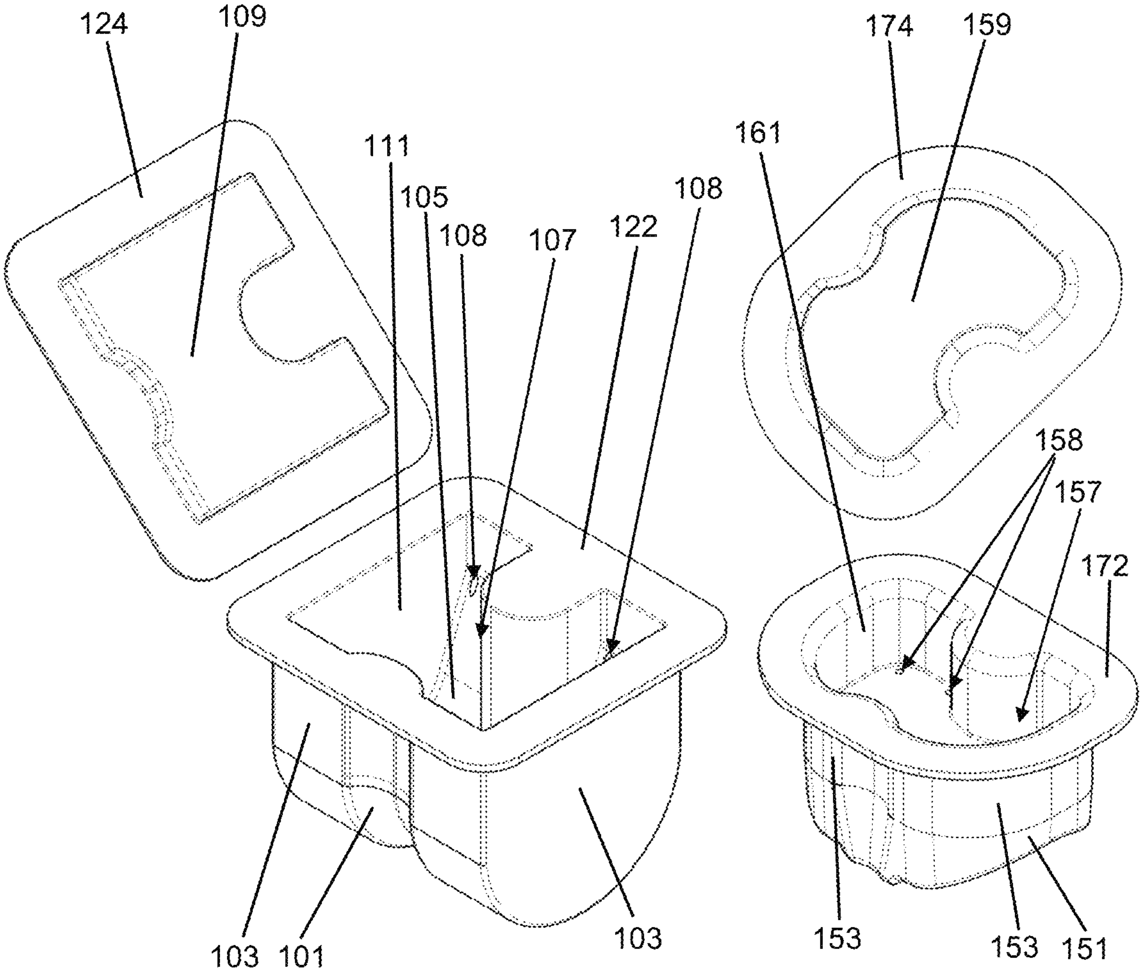
FIG. 24 shows a schematic perspective external view of the third exemplary embodiment according to FIG. 23 with open casting mold lower parts.
Figure 25:
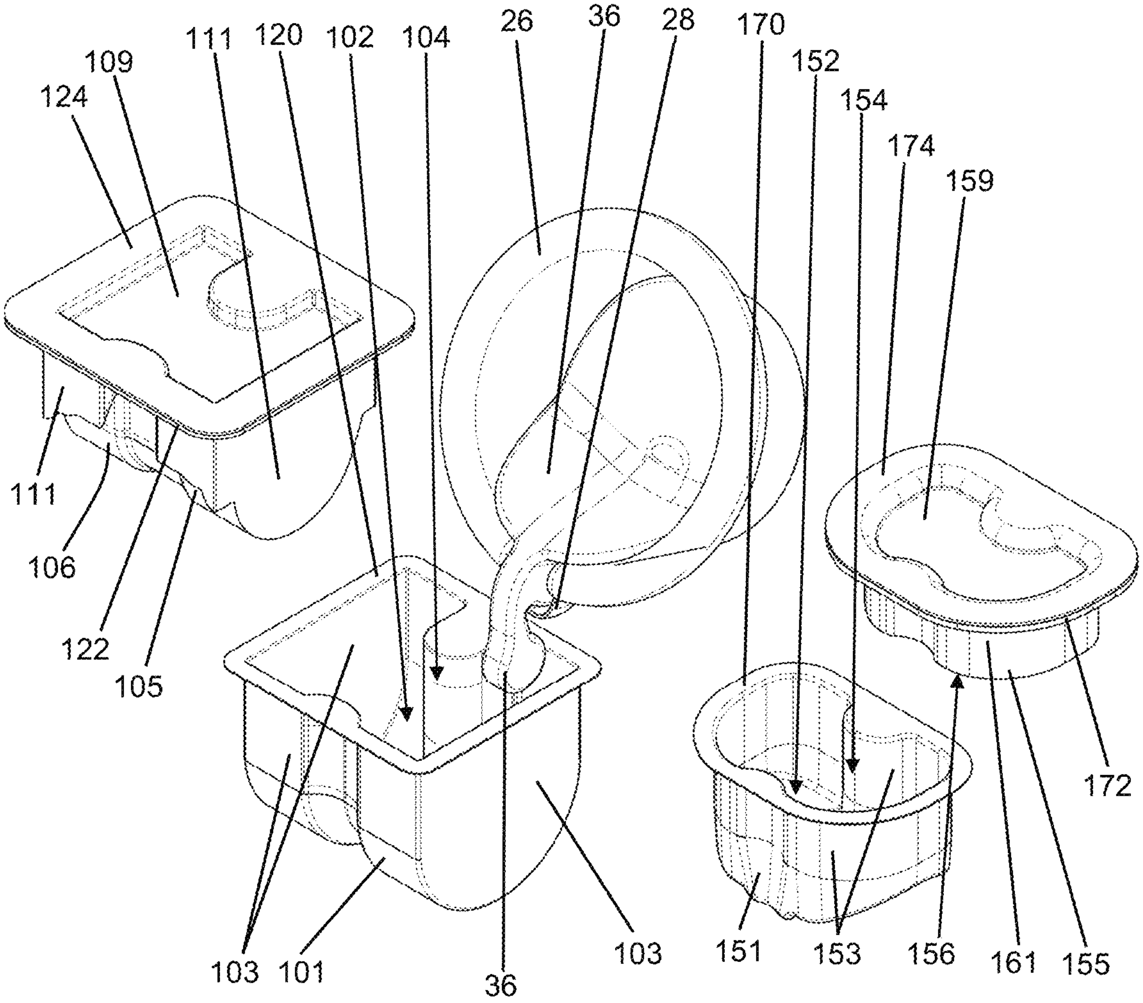
FIG. 25 shows a schematic perspective external view of the casting molds of the third exemplary embodiment during the introduction of bone cement paste.
Figure 26:
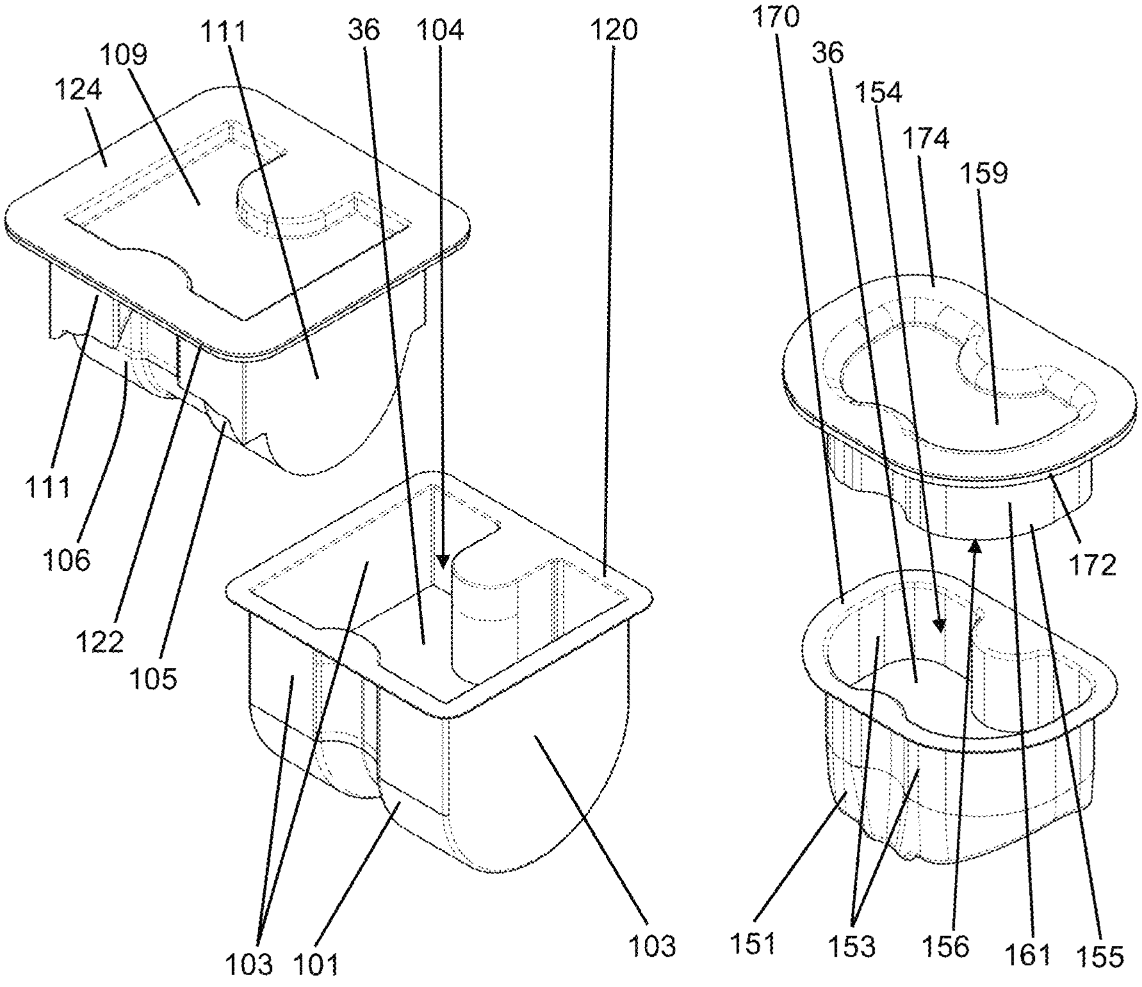
FIG. 26 shows a schematic perspective external view of the third exemplary embodiment prior to insertion of the casting mold upper parts into the casting mold lower parts.
Figure 27:
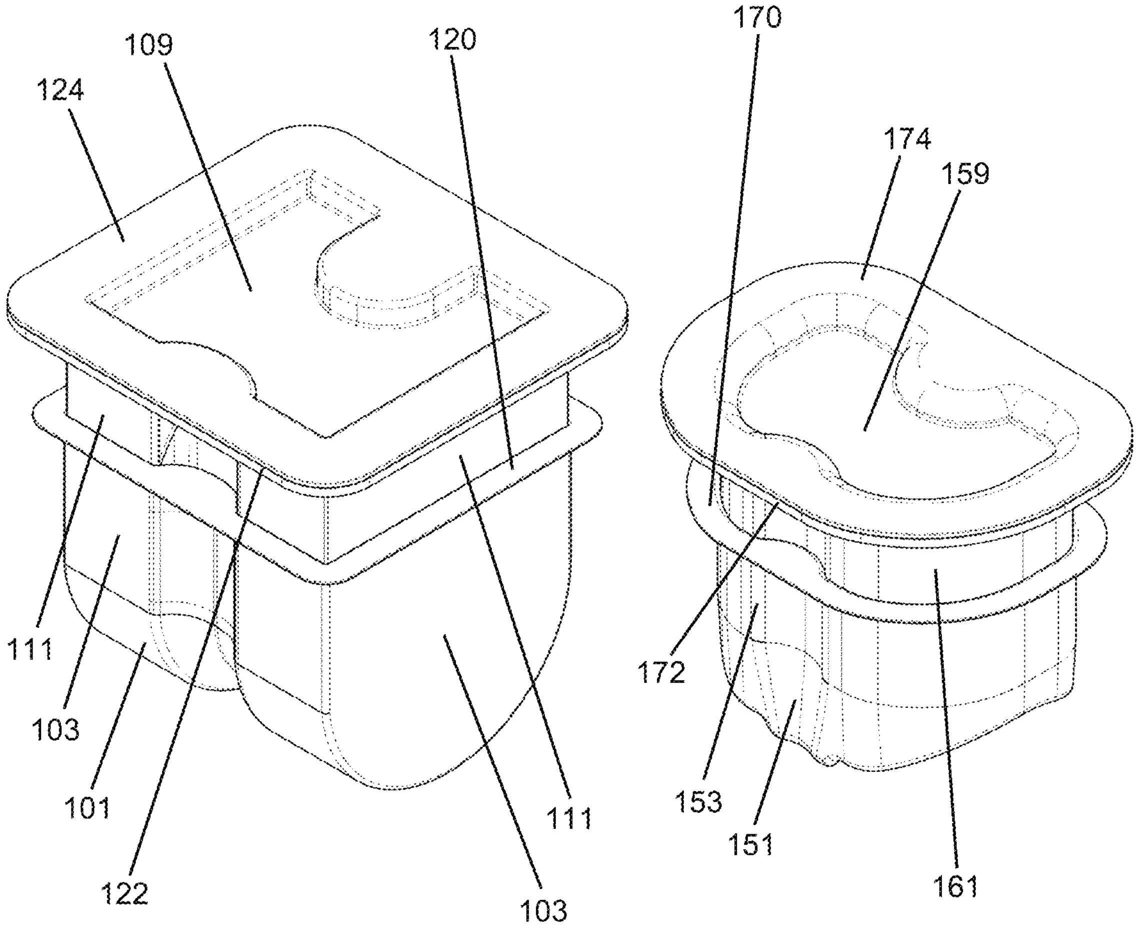
FIG. 27 shows a schematic perspective external view of the third exemplary embodiment during insertion of the casting mold upper parts into the casting mold lower parts.

The device may firstly be removed from a package (not shown) in a sterile state and may then be present as shown in FIG. 23 or in FIG. 25. The casting mold lower parts 101, 105 may optionally be inserted into the stands 116, 166, if stands 116, 166 are present.

The bone cement paste 36 may be mixed by mixing the cement powder from the film pouch 30 and the monomer liquid from the ampoule 32 in the mixing cup 26 with the assistance of the spatula 34. Alternatively, the bone cement paste 36 may also be produced in any other manner.

The bone cement paste 36 can then be introduced in each case in excess into the interior 104 and the cavity 102 and into the interior 154 and the cavity 152 (see FIG. 25). The casting mold upper part 105 may then be inserted and pushed into the casting mold lower part 101 and the casting mold upper part 155 into the casting mold lower part 151. The container 107 may to this end be closed with the lid 109 and the container 157 with the lid 159 (see FIGS. 26 and 27).

Figure 28:
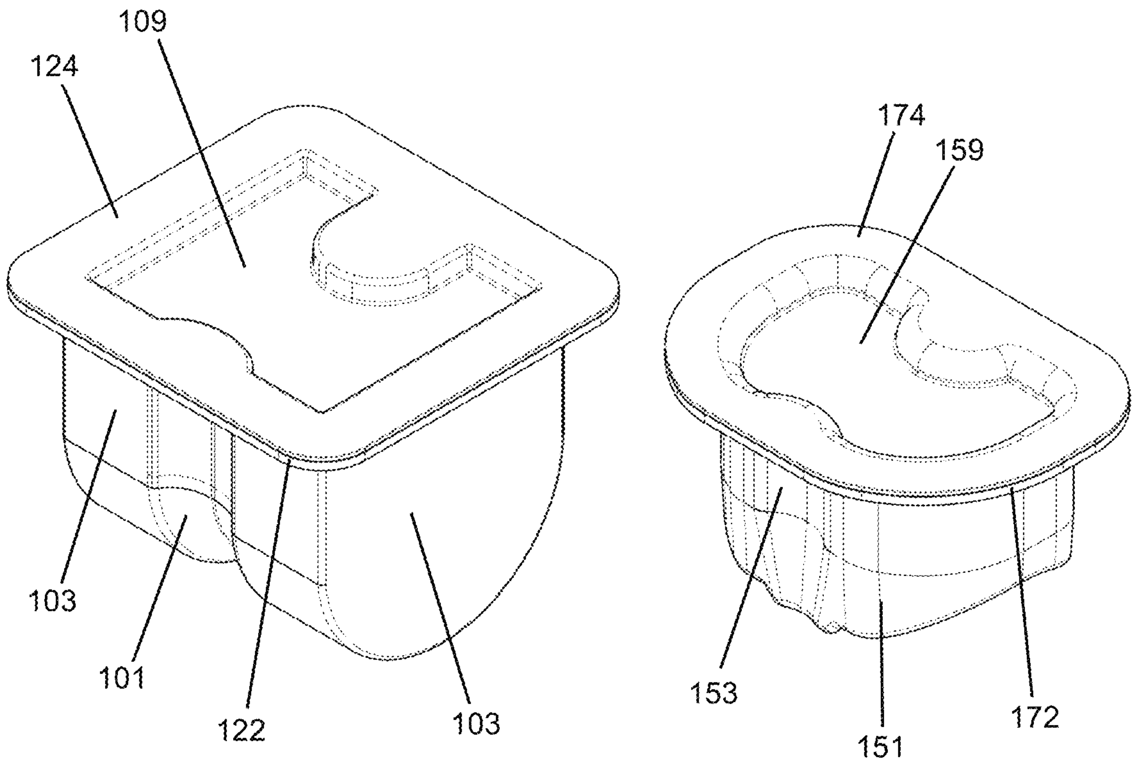
FIG. 28 shows a schematic perspective view onto the closed casting molds of the third exemplary embodiment.
Figure 29:
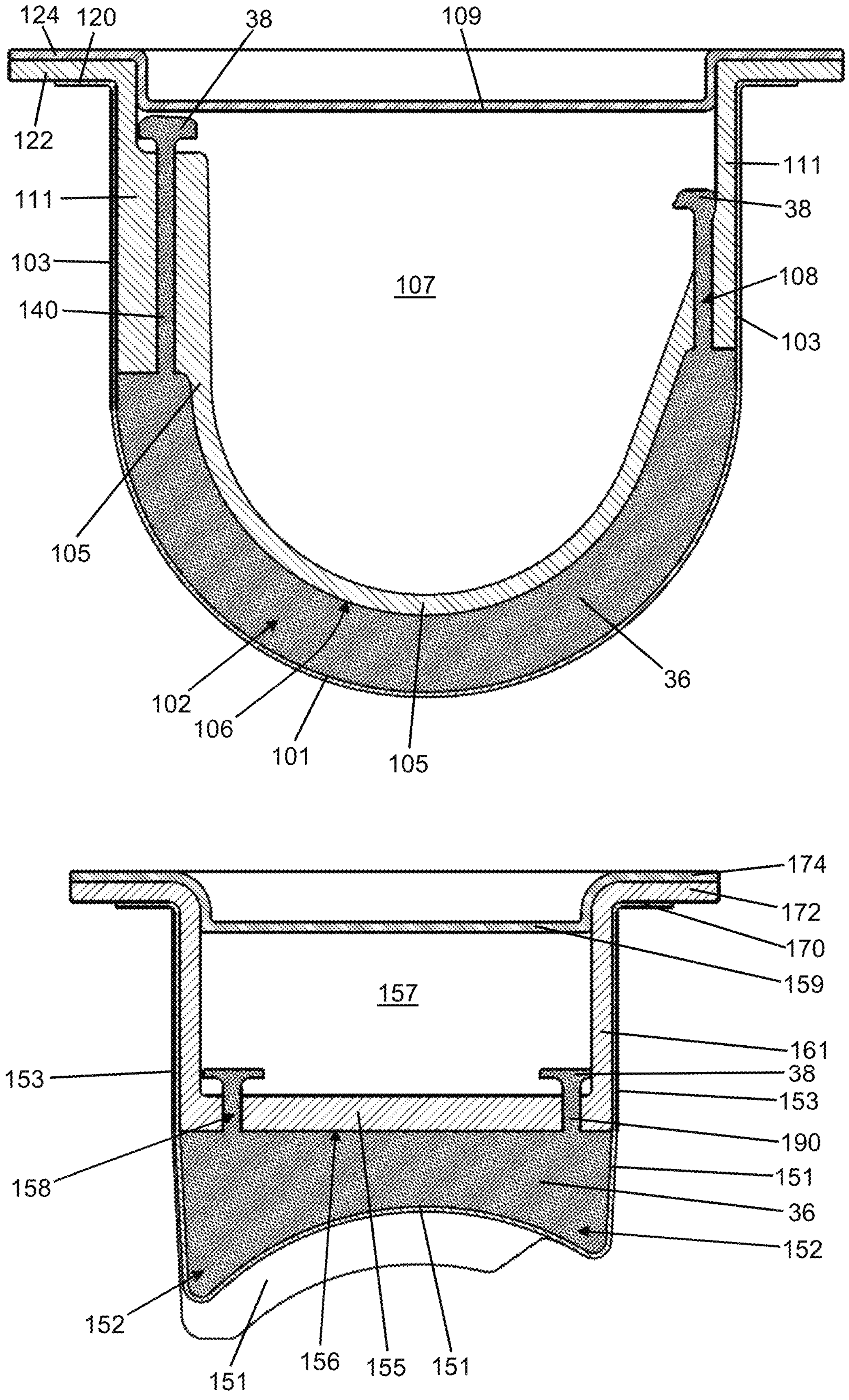
FIG. 29 shows a schematic perspective cross-sectional view of the casting molds filled with bone cement paste of the third exemplary embodiment in the closed state.
Figure 30:
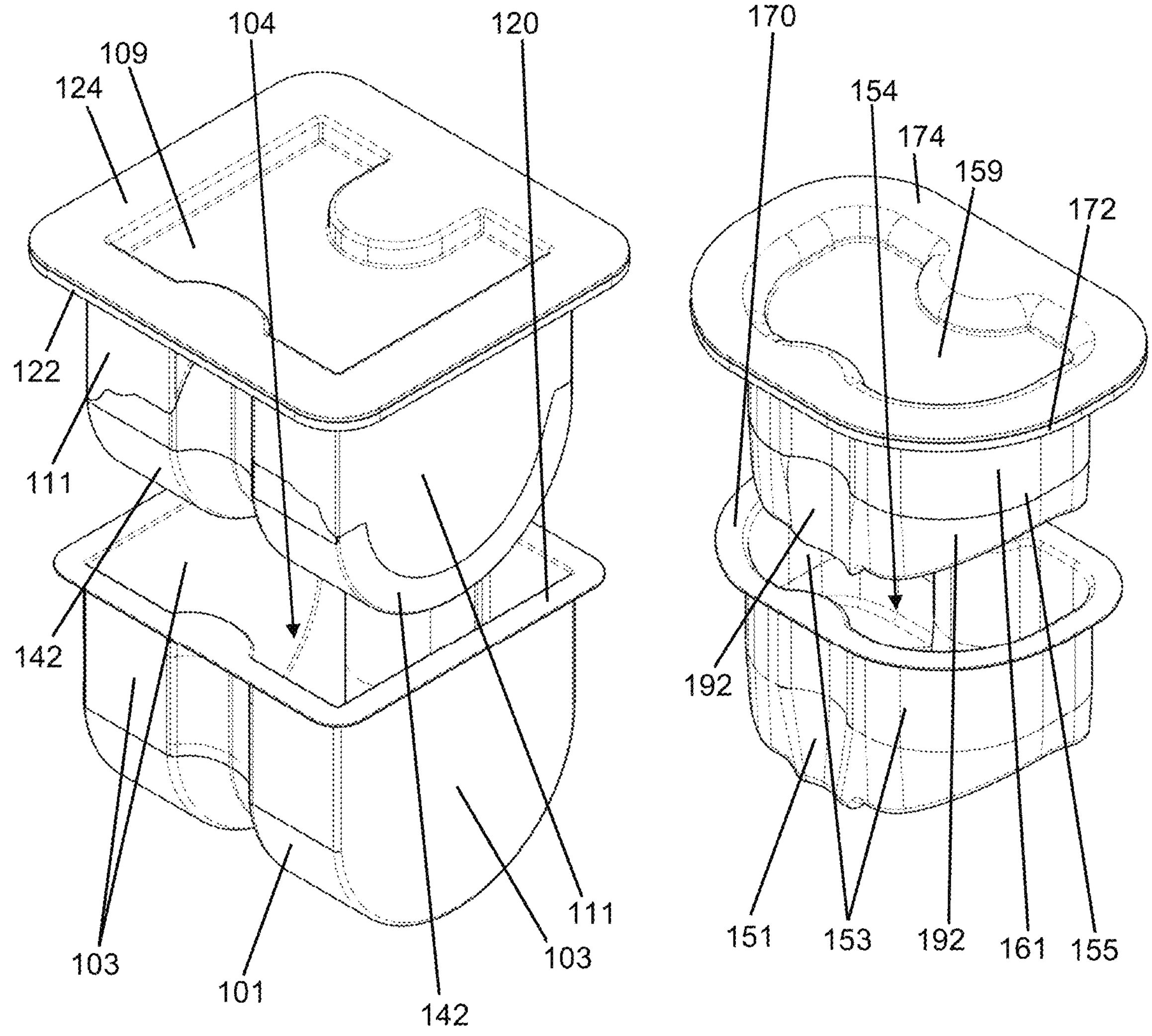
FIG. 30 shows a schematic perspective external view of the third exemplary embodiment during withdrawal of the casting mold upper parts from the casting mold lower parts.

The casting mold upper part 105 may be pushed into the interior 104 of the casting mold lower part 101 until the mating stop 122 rests against the limit stop 120, and the casting mold upper part 155 may be pushed into the interior 154 of casting mold lower part 151 until the mating stop 172 rests against the limit stop 170 (see in this regard FIGS. 28 and 29). When the casting mold upper parts 105, 155 are pushed in, the bone cement paste 36 which is present may be pressed into the cavities 102, 152 and the volume within the femoral component casting mold and the tibial component casting mold continuously decreases. Excess bone cement paste 38 is pressed out through the openings 108, 158 into the containers 107, 157 (see FIG. 29). The excess bone cement paste 38 can be enclosed in the containers 107, 157 with the assistance of the lids 109, 159.

Figure 31:
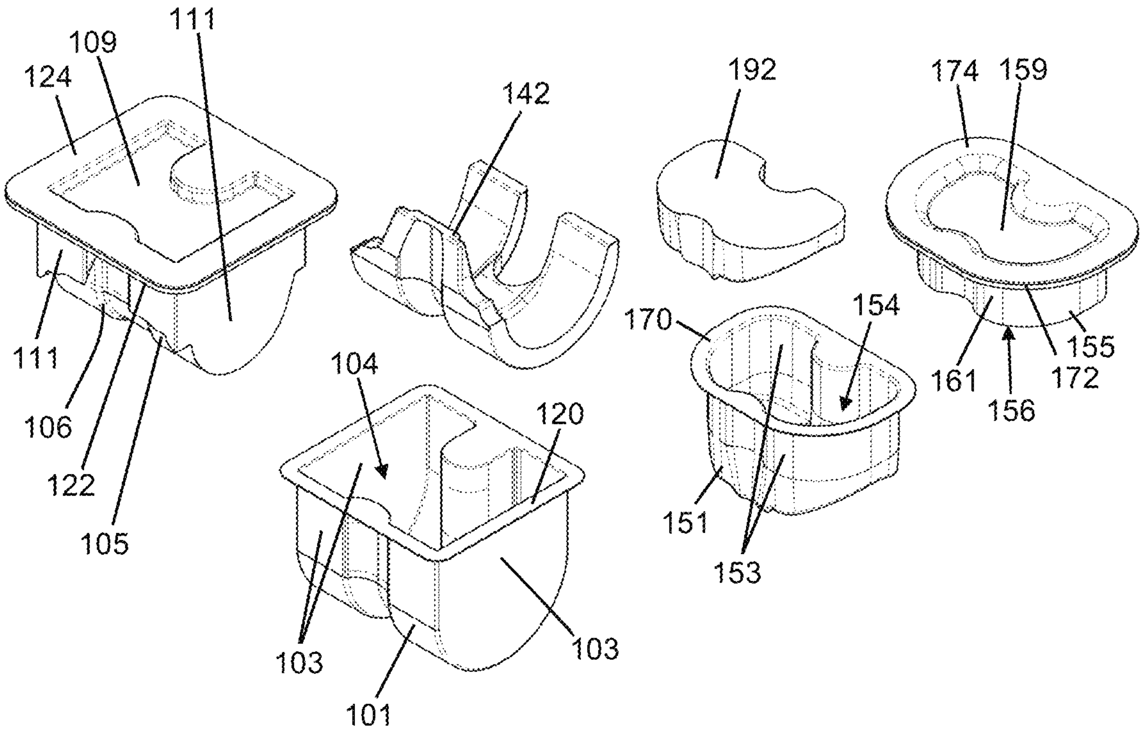
FIG. 31 shows a schematic perspective view onto the individual parts of the third exemplary embodiment with the two spacers for the knee joint.
Figure 34:
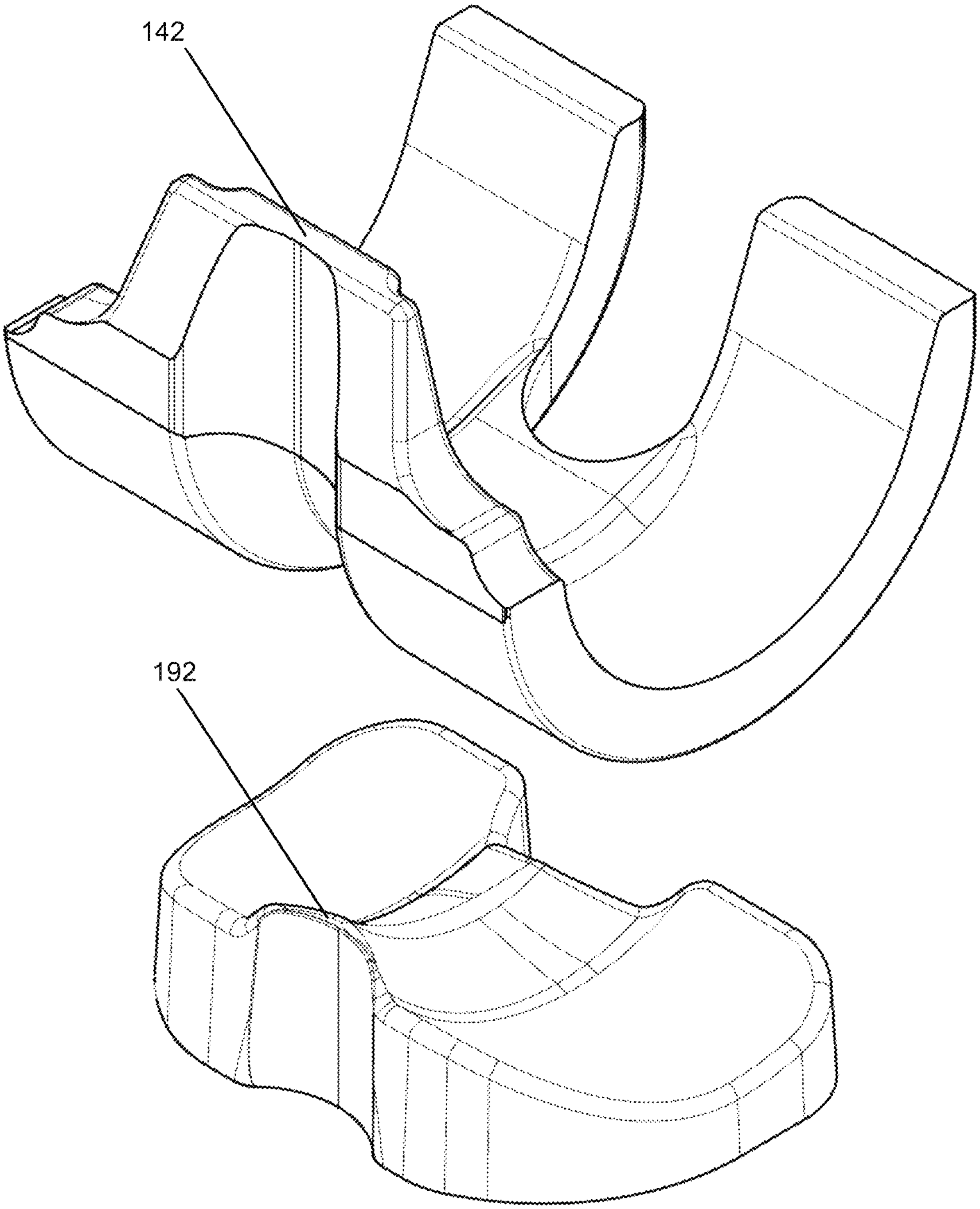
FIG. 34 shows a schematic perspective view onto the two parts of the spacer which have been produced using the device according to the third exemplary embodiment.
Figure 35:
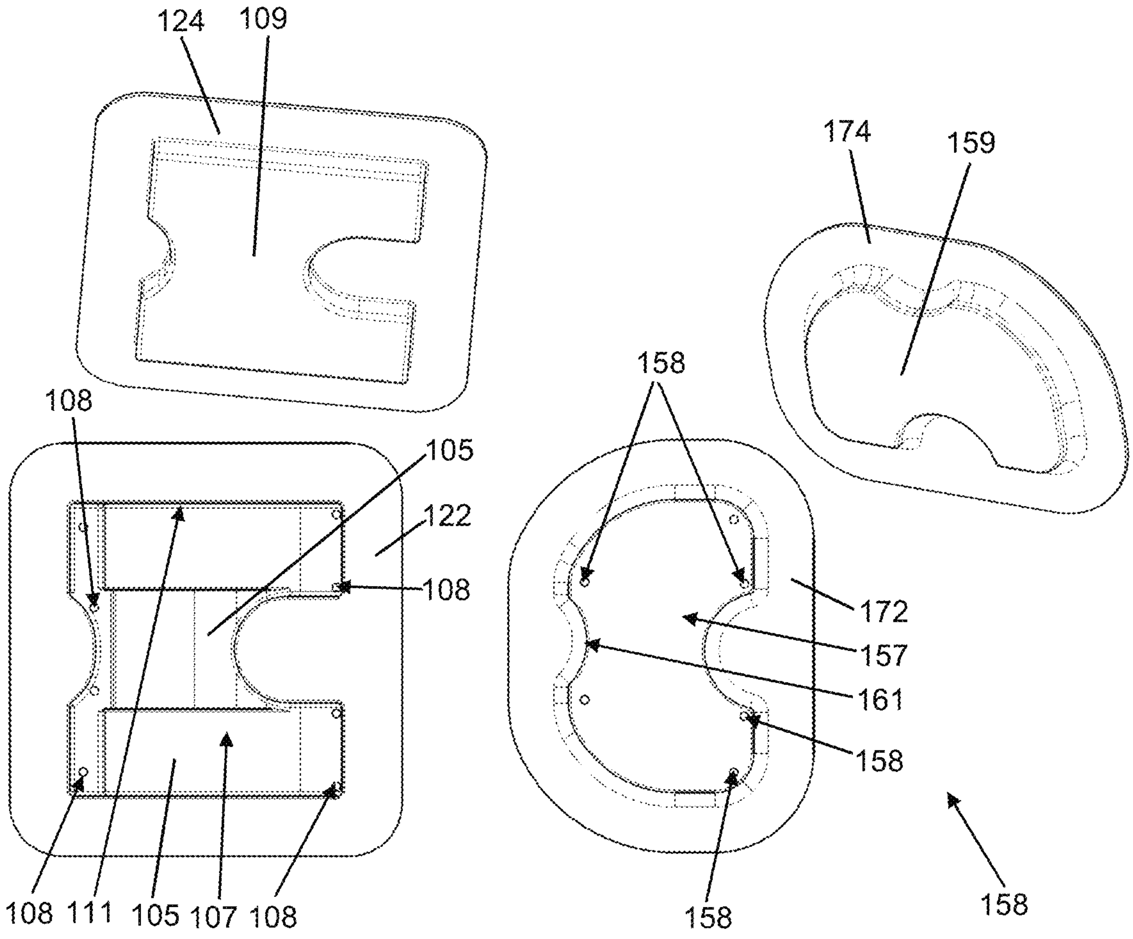
FIG. 35 shows a schematic plan view onto the casting molds with removed lid of the third exemplary embodiment.

The bone cement paste 36 in the femoral component casting mold and the tibial component casting mold may then cure, wherein the surface thereof is molded by the surface of the cavity 102 of the casting mold lower part 101 and the shaping surface 106 of the casting mold upper part 105 or by the surface of the cavity 152 of the casting mold lower part 151 and the shaping surface 156 of the casting mold upper part 155. The spacer 142 for the femur and the spacer 192 for the tibia, as shown for example in FIGS. 31 and 34, are obtained as a result. During curing of the bone cement paste 36, sprues 140, which connect the spacer 142 for the femur with the cured excess bone cement paste 38 in the container 107, may be formed in the openings 108. Likewise during curing of the bone cement paste 36, sprues 190, which connect the spacer 192 for the tibia with the cured excess bone cement paste 38 in the container 157, may be formed in the openings 158. The spacers 142, 192 are demolded by being detached from the casting mold lower parts 101, 151 and the casting mold upper parts 105, 155. In so doing, the sprues 140, 190 may be sheared off or broken off. In order to ensure straightforward demolding, the sprues 140, 190 must be of such a small diameter that they can be broken off or sheared off manually when the spacers 142, 192 are separated from the casting mold upper parts 105, 155. It has proven effective to this end for the sprues 140, 190 to have a diameter of a maximum of 2.5 cm and preferably of a maximum of 2 cm. Accordingly, the openings 8 should have an internal diameter of a maximum of 2.5 cm and preferably a maximum of 2 cm. Smaller diameters may also be selected in order to further simplify separation of the sprues 140, 190. The openings 108, 158 should, however, not have a diameter of less than 0.2 mm so that the bone cement paste 36 can still be pressed out through the openings 108, 158 without excessive resistance. Otherwise, depending on the viscosity of the bone cement paste 36, the resistance when pushing the casting mold upper part 105 into the casting mold lower part 101 or when pushing the casting mold upper part 155 into the casting mold lower part 151 may become too great for it still to be possible to be carried out manually or for damage to or destruction of the femoral component casting mold and the tibial component casting mold to be avoided. The optimum diameter of the openings 108, 158 here depends on the viscosity of the bone cement paste 36 which is used. Highly suitable diameters for typical bone cements are between 1 mm and 20 mm. As a rule of thumb, the higher the viscosity of the bone cement paste 36, the larger the selected internal diameter of the openings 108, 158 should be.

After demolding, any flash which has formed at the junctions between the casting mold lower parts 101, 151 and the casting mold upper parts 105, 155, and protruding residues of the sprues 140, 190 may be removed, for example by being trimmed off with a knife or scalpel or by being ground off with a grinding head. The spacers 142, 192, as shown in FIG. 34, are obtained as the final result.

The features of the invention disclosed in the preceding description, as well as in the claims, figures and exemplary embodiments, may be essential both individually and in any combination for realizing the invention in its various embodiments.

LIST OF REFERENCE SIGNS

1, 51, 101, 151 Casting mold lower part
2, 52, 102, 152 Cavity
3, 53, 103, 153 Casting mold wall
4, 54, 104, 154 Interior
5, 55, 105, 155 Casting mold upper part
6, 56, 106, 156 Shaping surface
7, 57, 107, 157 Container
8, 58, 108, 158 Opening
9, 59, 109, 159 Lid
10, 60 Metal core
11, 61, 111, 161 Internal wall
12, 62 Spacing piece
14 Bore
16, 66, 116, 166 Stand
18, 68 Groove
19, 69 Sprue
20, 70, 120, 170 Limit stop/contact surface
21, 71 Groove
22, 72, 122, 172 Mating stop/contact surface
23, 73 Recess
24, 74, 124, 174 Lid edge
26 Mixing cup
28 Spout
30 Film pouch containing bone cement powder
32 Ampoule containing monomer liquid
34 Spatula
36 Bone cement paste
38 Excess bone cement paste
40, 90, 140, 190 Sprue
42, 92, 142, 192 Spacer
44, 94 Spacer head
46, 96 Stem

The invention claimed is:

1. A device for producing a spacer by curing bone cement paste in a casting mold, wherein the spacer is provided to temporarily replace a joint or a part of a joint comprising an articulating surface of the joint in the medical field, to temporarily replace a hip joint, a knee joint or a shoulder joint, the device having

- a casting mold lower part, wherein the casting mold lower part has a cavity for receiving a bone cement paste and for molding a first surface region of the spacer from the bone cement paste;
- a casting mold wall which extends peripherally from a peripheral edge of the cavity of the casting mold lower part away from the cavity and which is open on a side opposite from the cavity, such that the cavity is accessible through an interior delimited by the casting mold wall;
- a casting mold upper part, wherein the casting mold upper part has a shaping surface for molding a second surface region of the spacer from the bone cement paste, wherein the casting mold upper part is insertable through an open side of the casting mold wall opposite from the cavity into the interior and is displaceable in a direction of the cavity, such that a hollow space is formed which is delimited by the cavity of the casting mold lower part, the shaping surface of the casting mold upper part and the casting mold wall and in which the spacer is moldable;

at least one container for receiving excess bone cement paste; and at least one opening in the shaping surface of the casting mold upper part and/or in the cavity of the casting mold lower, wherein the at least one opening opens into the at least one container for receiving excess bone cement paste, wherein the device has one or two lid(s), with which the casting mold upper part is closed or closable to an outside on a side opposite from the shaping surface of the casting mold upper part, such that an upper container closed to the outside is formed as one of the at least one containers for receiving bone cement paste between the casting mold upper part and the lid, and/or with which the casting mold lower part is closed or closable to the outside on the side opposite from the cavity of the casting mold lower part, such that a lower container closed to the outside is formed as one of the at least one containers for receiving bone cement paste between the casting mold lower part and the lid, wherein the one or two lid(s) is placed or placeable into or onto the casting mold upper part or into or onto an internal wall of the casting mold upper part in order to close the side opposite from the shaping surface of the casting mold upper part to the outside and there form a closed container for receiving excess bone cement paste, and/or the or one of the lid(s) is placed or placeable into or onto the casting mold lower part in order to close the side opposite from the cavity of the casting mold lower part to the outside and there forms a closed container for receiving excess bone cement paste;

wherein the container for receiving bone cement paste is impermeably closed to the outside for the bone cement paste; and wherein the lid or lids are gas-permeably closed with the casting mold upper part such that air can escape from the upper or lower container delimited with the lid or lids when the bone cement paste flows through the at least one opening while containing the bone cement between the casting mold and the lid or lids.

2. The device according to claim 1, characterized in that mutually opposing parts of the casting mold wall are oriented parallel to one another or the casting mold wall tapers slightly conically in the direction of the cavity or the casting mold wall has a shape of a right or skewed general cylinder, a base area of which is delimited by the peripheral edge of the cavity.

3. The device according to claim 1, characterized in that the internal wall of the casting mold upper part extends peripherally from a peripheral edge of the shaping surface of the casting mold upper part away from the cavity of the casting mold lower part.

4. The device according to claim 3, characterized in that the internal wall and the casting mold wall rest flush against one another when the casting mold upper part is pushed into the casting mold wall and/or the internal wall forms a seal against the casting mold wall for the bone cement paste when the casting mold upper part is pushed into the casting mold wall.

5. The device according to claim 1, characterized in that the lid or lids has at least one vent opening.

6. The device according to claim 1, characterized in that a volume of the cavity of the casting mold lower part and a volume delimited by the casting mold wall together are larger than a volume of the spacer to be produced.

7. The device according to claim 1, characterized in that the casting mold wall and the casting mold lower part are formed as one part.

8. The device according to claim 1, characterized in that the device has a mixing system for mixing bone cement paste, a cement powder and a monomer liquid, wherein the cement powder and the monomer liquid are stored separately from one another, wherein the bone cement paste is mixable from the cement powder and the monomer liquid with assistance of the mixing system.

9. The device according to claim 8, characterized in that the mixing system includes a mixing cup which has a spout for introducing the bone cement paste from the mixing cup into the cavity and the interior delimited by the casting mold wall, or the mixing system is a bone cement cartridge for storing and mixing the cement powder and the monomer liquid and for delivering mixed bone cement paste from the bone cement cartridge.

10. The device according to claim 1, characterized in that the casting mold lower part and the casting mold upper part, and the lid or lids consist of a plastics film or substantially consist of a plastics film or the casting mold lower part and the casting mold upper part, and the lid or lids are in each case composed of two or more plastics films which are connected together or are welded or adhesively bonded together.

11. The device according to claim 1, characterized in that the casting mold lower part, the casting mold upper part and the casting mold wall and the lid or lids substantially or entirely consist of a plastics material or are fabricated from a polyolefin, polyethylene (PE) or polypropylene (PP) or from a PETG film and/or a polyamide film and/or a PE film.

12. The device according to claim 1, characterized in that the at least one opening has a minimum cross-sectional length of a maximum of 2.5 mm, and/or the at least one opening has a minimum cross-sectional length of at least 0.2 mm.

13. The device according to claim 1, characterized in that, at the end of the casting mold wall opposite from the cavity of the casting mold lower part, a limit stop is arranged for limiting the movement of the casting mold upper part within the casting mold wall in the direction of the cavity, wherein a contact surface is arranged as a limit stop at the end of the casting mold wall opposite from the cavity of the casting mold lower part.

14. The device according to claim 1, characterized in that the device has a metal core which is to be or is arranged in the cavity, wherein the device has a plurality of spacing pieces which keep the metal core in the cavity spaced from an internal side of the cavity and from an internal side of the casting mold wall.

15. The device according to claim 1, characterized in that the casting mold lower part or the casting mold lower part and the casting mold wall or the casting mold lower part, the casting mold wall and the casting mold upper part is or are transparent or translucent.

16. The device according to claim 1, characterized in that the at least one opening is arranged in regions which, in a normal disposition of the casting mold, are highest points of the hollow space.

17. The device according to claim 1, characterized in that the shaping surface of the casting mold upper part rests with an outer edge internally against the casting mold wall and, when the casting mold upper part is pushed in, the edge slides internally on the casting mold wall.

18. The device according to claim 1, characterized in that the device has a stand, wherein the casting mold lower part is insertable into the stand and the stand is designed, with the casting mold lower part therein, to be placed on a flat support.

19. A method for producing a spacer for temporarily replacing a joint or part of a joint, for example a hip joint, a knee joint or a shoulder joint, comprising an articulating surface of the joint, wherein the method is carried out with the device according to claim 1, the method having the following chronological steps:

A) introduction of flowable bone cement paste into the cavity and the interior delimited by the casting mold wall, wherein a larger volume of the flowable bone cement paste is introduced than is required by the spacer;

B) insertion of the casting mold upper part into the casting mold wall, wherein the shaping surface points in a direction of the cavity;

C) pushing in of the casting mold upper part in the direction of the cavity within the casting mold wall;

D) emergence of excess bone cement paste through the at least one opening as the casting mold upper part continues to be pushed in, wherein the excess bone cement paste flows into the at least one container for receiving the excess bone cement paste;

E) completion of pushing in when a limit stop is reached or when a desired height of the spacer is reached;

F) curing of the bone cement paste in the hollow space formed by the cavity, the shaping surface of the casting mold upper part and the casting mold wall and G) removal of the spacer molded and cured in this manner from the hollow space, wherein sprues of the cured bone cement paste formed in the at least one opening are detached.

20. The method according to claim 19, characterized in that, in step D), the excess bone cement paste flows into a lower container closed by a lid for receiving the excess bone cement paste on the casting mold lower part and is enclosed therein and/or flows into an upper container closed by a lid for receiving the excess bone cement paste on the casting mold upper part and is enclosed therein, wherein, on demolding the cured spacer after step F) or in step G), the cured excess bone cement paste remains in the lower container and/or the upper container.

21. The method according to claim 19, characterized in that, before step A), the bone cement paste is mixed from a monomer liquid and a cement powder.

22. The method according to claim 19, characterized in that, before step A), a metal core is arranged in the cavity, wherein the metal core is spaced from the internal wall of the cavity and the casting mold wall with assistance of pin-shaped spacing pieces.

23. The method according to claim 19, characterized in that, during step C), the air is expelled through the at least one opening from the hollow space delimited by the cavity of the casting mold lower part, the shaping surface of the casting mold upper part and the casting mold wall.

24. The method according to claim 19, characterized in that, after step F) and before step G), the casting mold upper part is withdrawn from the open end of the casting mold wall.

25. The device according to claim 3, characterized in that the internal wall at least in places delimits the at least one container and/or mutually opposing parts of the internal wall are oriented parallel to one another or the internal wall has a shape of a right or skewed general cylinder, a base area of which is delimited by the peripheral edge of the shaping surface of the casting mold upper part.

* * * * *